US006476388B1

United States Patent
Nakagaki et al.

(10) Patent No.: US 6,476,388 B1
(45) Date of Patent: Nov. 5, 2002

(54) SCANNING ELECTRON MICROSCOPE HAVING MAGNIFICATION SWITCHING CONTROL

(75) Inventors: Ryo Nakagaki, Kawasaki; Yuji Takagi, Kamakura; Atsushi Shimoda, Hiratsuka; Kenji Obara, Yokohama; Yasuhiko Ozawa, Abiko; Hideka Bamba, Okazaki; Seiji Isogai, Hitachinaka; Kenji Watanabe, Oume; Chie Shishido, Yokohama; Toshiei Kurosaki, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/421,093

(22) Filed: Oct. 19, 1999

(30) Foreign Application Priority Data

Oct. 19, 1998 (JP) .......................................... 10-296481
Oct. 27, 1998 (JP) .......................................... 10-304926

(51) Int. Cl.[7] ............................ G21K 7/00; G01N 23/00
(52) U.S. Cl. ..................... 250/310; 250/311; 250/307; 250/306; 324/751
(58) Field of Search ............................... 250/307, 310, 250/311, 306; 324/751

(56) References Cited

U.S. PATENT DOCUMENTS

| | | | | |
|---|---|---|---|---|
| 4,169,240 A | * | 9/1979 | Anderson et al. | 315/382 |
| 4,199,681 A | * | 4/1980 | Namae | 250/311 |
| 4,880,977 A | * | 11/1989 | Tomita et al. | 250/311 |
| 5,750,990 A | * | 5/1998 | Mizuno et al. | 250/307 |
| 5,834,774 A | * | 11/1998 | Negishi et al. | 250/310 |
| 5,912,462 A | * | 6/1999 | Takami et al. | 250/310 |
| 5,959,459 A | * | 9/1999 | Satya et al. | 324/751 |

FOREIGN PATENT DOCUMENTS

| JP | 5-223747 | 8/1993 |
|---|---|---|
| JP | 6-249790 | 9/1994 |

OTHER PUBLICATIONS

"Bit Supplement", Calculus Geometry and Geographical Information Processing, pp. 110–121.

* cited by examiner

Primary Examiner—John R. Lee
Assistant Examiner—Kalimah Fernandez
(74) Attorney, Agent, or Firm—Antonelli, Terry, Stout & Kraus, LLP

(57) ABSTRACT

The invention is a scanning electron microscope including a switching control unit for controlling to switch at least scanning unit to switch a digital image signal of a low magnification based on a wide image taking field of view to and from a digital image signal of a high magnification based on a narrow image taking field of view from an A/D conversion unit and a beam spot diameter control unit for controlling to switch a spot diameter of electron beam on a surface of an object substrate in controlling to switch the signals by the switching control unit and a defect portion analyzing method using the scanning electron microscope.

9 Claims, 25 Drawing Sheets

301 IMAGE TAKING AREA

FIG. 14a

| PRODUCT NAME | PRESENCE OR ABSENCE OF MEMORY CELL | CELL PITCH | IMAGE TAKING MAGNIFICATION (UPPER : LOW MAGNI- FICATION) (LOW : HIGH MAGNI- FICATION) | CONTROL CONDITION (UPPER : LOW MAGNI- FICATION) (LOW : HIGH MAGNI- FICATION) |
|---|---|---|---|---|
| MEMORY A | PRESENCE | 5μm | X10,000 | CONTROL CONDITION 3 |
| | | | X50,000 | CONTROL CONDITION 1 |
| MEMORY B | PRESENCE | 15μm | X10,000 | CONTROL CONDITION 2 |
| | | | X30,000 | CONTROL CONDITION 1 |
| LOGIC C | ABSENCE | | X10,000 | CONTROL CONDITION 1 |
| | | | X50,000 | CONTROL CONDITION 1 |
| LOGIC D | ABSENCE | | X10,000 | CONTROL CONDITION 1 |
| | | | X50,000 | CONTROL CONDITION 1 |
| LOGIC E MIXED WITH MEMORY | PRESENCE | 15μm | X10,000 | CONTROL CONDITION 2 |
| | | | X30,000 | CONTROL CONDITION 1 |

FIG. 14b

| CONTROL ITEM / CONDITION | STAGE Z-DIRECTION POSITION | BEAM CURRENT | ・・・・・ |
|---|---|---|---|
| CONTROL CONDITION 1 | 0 [mm] | 1.0 [pA] | ・・・・・ |
| CONTROL CONDITION 2 | 10 [mm] | 1.5 [pA] | ・・・・・ |
| CONTROL CONDITION 3 | 20 [mm] | 2.0 [pA] | ・・・・・ |
| ⋮ | ⋮ | ⋮ | ⋮ |

FIG. 15a

| | INPUT INFORMATION | | | | |
|---|---|---|---|---|---|
| | KIND OF SAMPLE | IMAGE TAKING POSITION | IMAGE TAK- ING MAGNI- FICATION | • • • • • | |
| IMAGE TAKING CONDITION 1 | k 1 | p 1 | m 1 | | → CONTROL PATTERN 1 |
| IMAGE TAKING CONDITION 2 | k 2 | p 2 | m 1 | | → CONTROL PATTERN 2 |
| IMAGE TAKING CONDITION 3 | k 1 | p 3 | m 2 | | → CONTROL PATTERN 1 |
| IMAGE TAKING CONDITION 4 | k 3 | p 4 | m 2 | | → CONTROL PATTERN 3 |
| ⋮ | ⋮ | ⋮ | ⋮ | ⋮ | ⋮ |

FIG. 15b

| | STAGE MOVEMENT DISTANCE | NUMERICAL APERTURE OF OBJEC- TIVE LENS | BEAM CURRENT | ANALOG FILTER | DIGITAL FILTER |
|---|---|---|---|---|---|
| CONTROL PATTERN 1 | a 1 | b 1 | c 1 | d 1 | e 1 |
| CONTROL PATTERN 2 | a 2 | b 2 | c 2 | d 2 | e 2 |
| ⋮ | ⋮ | ⋮ | ⋮ | ⋮ | ⋮ |
| CONTROL PATTERN N | a N | b N | c N | d N | e N |

FIG. 20

|  | ALIGNMENT NO. | DEFECT SAMPLING MAGNIFICATION |
|---|---|---|
| DEFECT INSPECTING APPARATUS A | 5 | 3 0 0 0 |
| DEFECT INSPECTING APPARATUS B | 7 | 5 0 0 0 |
| DEFECT INSPECTING APPARATUS C | 5 | 7 0 0 0 |
| DEFECT INSPECTING APPARATUS D | 1 0 | 4 0 0 0 |

SCANNING ELECTRON MICROSCOPE HAVING MAGNIFICATION SWITCHING CONTROL

BACKGROUND OF THE INVENTION

The present invention relates to a scanning electron microscope capable of acquiring electron beam image having high resolution in respect of various defect portions present on an object substrate (sample) such as various semiconductor substrates or the like and analyzing characteristic amounts or properties of defect portions based on the acquired electron beam image having high resolution, and a method of analyzing defect portions using the same as well as an automatic image sampling apparatus having a scanning electron microscope preferable for efficiently carrying out review of defects particularly in semiconductor fabrication process.

In recent years, progress of miniaturization of a circuit pattern formed on an object substrate (sample) such as various semiconductor substrates or the like has been remarkable and there is a case in which a defect size of an object to be observed is smaller than the wavelength of light. Hence, in place of optical observation, there has been carried out defect observation using image by a scanning electron microscope. However, when a defect image is taken by a scanning electron microscope, there poses a problem in which even when an object substrate is moved to a position of a defect detected by an appearance inspecting apparatus, the defect which is an object to be observed in the field of view is not present.

The reason is that in addition to a difference in coordinate control between the appearance inspecting apparatus and the scanning electron microscope, an error in accuracy of a sample stage for each of the appearance inspecting apparatus and the scanning electron microscope and so on, the magnification of image taking is much higher than optical magnification in the appearance inspecting apparatus and the field of view is narrow.

Hence, when a foreign particles is observed by a scanning electron microscope, the foreign particle can be discovered most efficiently when low magnification so that a search area is brought into the field of view in one operation, is selected. However, when a size of the foreign particle is small, there is a case that presence of the foreign particle is not noticed with low magnification. Hence, according to Japanese Patent Laid-open No. 5-223747 (prior art 1), in a foreign particle observing apparatus having an optical inspecting device of a foreign particle on a wafer surface and its similar device and an electron microscope for carrying out shape observation or analysis of foreign particle, defects or the like by using wafer coordinates and foreign particle information provided by the devices, there are provided means for determining a level of a size of a foreign particle provided by the optical inspecting device and its similar device and means for dividing an observation area of the wafer into N×M of divided areas when the foreign particle level is equal to or smaller than a constant value and dividedly observing the respective divided areas by the electron microscope.

In the meantime, a microscope starting from a scanning electron microscope has various objects of image taking and magnification for taking image thereof has various values. It is very important to take image without causing pseudo noise even under the various conditions. When image is taken manually, an operating person always monitors whether or not pseudo noise is caused in taken image and when pseudo noise is caused, image can be taken again after erasing the noise. However, when observation by the microscope is not carried out manually, for example, when information on positions of a plurality of portions on a sample to be observed is previously inputted to a microscope and the plurality of portions are observed automatically to thereby acquire data of taken image, a control for preventing the above-described noise from being produced is required to be carried out automatically.

However, according to the prior art 1, sufficient consideration is not given to that image is taken without causing pseudo noise in respect of such various object substrates (image taken objects).

Further, according to the prior art 1, it is necessary to enlarge observation magnification to be able to observe fine defects and to search the fine defects over an observation area having M×N of the divided areas and wasteful search is obliged to be carried out. In particular, when a number of fine defects are present in an object substrate, an amount of wasteful search is significantly increased.

SUMMARY OF THE INVENTION

In order to solve the above-described problem, it is an object of the present invention to provide a scanning electron microscope capable of analyzing characteristic amounts or properties of a defect portion in respect of the defect portion by automatically specifying a position of the defect portion to accurately take an image thereof without generating pseudo noise on a provided digital image even when an image of any object substrate is taken by any magnification and a defect portion analyzing method using the same.

Further, it is other object of the present invention to provide an apparatus and a method of automatically sampling an image by a scanning electron microscope capable of analyzing characteristic amounts and properties (categories) thereof and so on by positioning the fine defect in an image taking field of view of a high magnification in a short period of time to acquire a digital image signal having a high resolution and to take an image of a fine defect with a high magnification.

In order to achieve the above-described object, the present invention is featured in a scanning electron microscope which provides an image taking magnification setting means for setting a magnification of image taking, and takes the image by controlling a spot diameter of irradiating beam on a sample by using information concerning image taking magnification set to the image taking magnification setting unit and background information at an image taking portion.

Further, the present invention is featured in a scanning electron microscope which provides an image taking magnification setting unit for setting magnification of image taking, and carries out a signal processing of a filtering processing or the like to an analog electric signal converted from an intensity of an electron beam signal of secondary electron, reflected electron or absorbed electron from an object substrate (sample) or a digital signal provided from the analog electric signal by using information concerning image taking magnification set to the image taking magnification setting unit and background information at an image taking portion.

Further, the present invention is featured in a scanning electron microscope which includes a switching control unit for controlling to switch at least scanning means so as to be obtained a digital image signal of a low magnification based on a wide image taking field of view and a digital image signal of a high magnification based a narrow image taking field of view being switched from an A/D conversion unit, and a beam spot diameter control unit for controlling to switch a spot diameter of an electron beam at a surface of an object substrate in controlling to switch the signals by the switching control unit or a beam spot diameter control unit for controlling the beam spot of the electron beam based on information concerning a surface texture on an image taking portion of the object substrate in taking an image thereof in a wide image taking field of view by controlling to switch the signals by the switching control unit.

Further, the present invention is featured in a scanning electron microscope which includes a switching control unit for controlling to switch at least scanning means so as to be obtained a digital image signal of a low magnification based on a wide image taking field of view and a digital image signal of a high magnification based on a narrow image taking field of view being switched from an A/D conversion unit, and a control unit for controlling so as to restrain pseudo noise components generated from an image taking portion of an object substrate in taking an image with a wide image taking field of view by controlling to switch the signals by the switching control unit, or a signal processing unit for reducing the pseudo noise components at high frequencies by carrying out a signal processing in accordance with a surface texture of the image taking portion of the object substrate to an analog image signal outputted from a detector or a digital image signal provided by the A/D conversion unit.

Further, the present invention is featured in a scanning electron microscope which includes position specifying means for positioning the defect portion in a wide image taking field of view based on the position coordinate of the defect portion present on an object substrate mounted on a stage, irradiating with the electron beam to scan the positioned defect portion in a defocused state or under a state in which pseudo noise components are restrained from being generated from a background such that a wide image taking field of view is provided, detecting an analog image signal from a detector, converting the detected analog image signal into a digital image signal of low magnification at the A/D conversion unit and specifying the position of the defect portion based on the converted digital image signal indicating the defect portion of the low magnification or the digital image signal indicating the defect portion of the low magnification so that the pseudo noise components at high frequencies are reduced, and analyzing means for positioning the defect portion in a narrow image taking field of view based on the position of the defect portion specified by the specifying means, irradiating with the electron beam to scan the positioned defect portion to provide the narrow taking image field in a focused state, detecting an analog image signal by the detector, converting the detected analog image signal into a digital image signal of the high magnification by the A/D conversion unit and analyzing characteristic amounts or properties of the defect portion based on the converted digital image signal indicating the defect portion of the high magnification.

Further, the present invention is an automatic image sampling apparatus which is a scanning electron microscope including a storing unit for storing a dimension of a defect present on an object substrate provided from an appearance inspecting apparatus and information on a first position coordinate thereof; and a means for positioning a large defect in a field of view of an image taking magnification of a low magnification provided by controlling scanning means based on the information concerning the first position coordinate with respect to the defect having a large dimension present on the object substrate provided from the storing unit, storing a digital signal of the large defect into the image storing unit by taking an image of the positioned large defect by the image taking magnification of the low magnification, calculating a second position coordinate of the defect based on the stored digital image signal of the large defect and calculating a deviation correction coefficient (a coordinate correction coefficient) from a relationship between the calculated second position coordinate and the first position coordinate, and its method.

Further, according to the present invention, there is provided the automatic image sampling apparatus and its method further including image sampling controlling means for calculating a second position coordinate by correcting a first position coordinate of a small defect provided from the storing unit by the deviation correction coefficient calculated by the deviation correcting coefficient calculating means with respect to the defect having a small dimension present on the object substrate provided from the storing unit, positioning the small defect in a field of view of an image taking magnification of a high magnification provided by controlling the scanning means based on information concerning the calculated second position coordinate and storing a digital image signal of the small defect into the image storing unit for sampling by taking an image of the positioned small defect by the image taking magnification of the high magnification.

Further, the present invention is an automatic image sampling apparatus which is a scanning electron microscope including a storing unit for storing a dimension of a defect present on an object substrate provided from an appearance inspecting apparatus and information on a first position coordinate thereof, first image sampling controlling means for positioning a large defect in a field of view of an image taking magnification of a low magnification provided by controlling scanning means based on the information concerning the first position coordinate of the defect having a large dimension present on the object substrate provided from the storing unit, storing a digital image signal of the large defect into the image storing unit by taking an image of the positioned large defect by the image taking magnification of the low magnification, calculating a second position coordinate of the defect and a size of the defect based on the digital image signal of the stored large defect, calculating a deviation correction coefficient from a relationship between the calculated second position coordinate and the first position coordinate, positioning the large defect in a field of view of an image taking magnification adapted to the calculated size of the defect, taking an image of the positioned large defect by the adapted image taking magnification and storing the digital image signal of the large defect into the image storing unit for sampling; and second image sampling controlling means for calculating a second position coordinate by correcting a first position coordinate of a small defect provided from the storing unit by the deviation correcting coefficient calculated by the first image sampling controlling means with respect to the defect having a small dimension present on the object substrate provided from the storing unit, positioning the small defect in a field of view of an image taking magnification of a high magnification provided by controlling the scanning means based on information concerning the calculated second position coordinate, taking an image of the positioned small defect by the image taking magnification of the high magnification and storing a digital image signal of the small defect into the image storing unit for sampling and its method.

Further, the present invention is an automatic image sampling apparatus which is a scanning electron microscope further including a storing unit for storing information concerning a dimension of a defect present on an object substrate and a position coordinate thereof and information concerning a circuit pattern at an area on the object substrate; and a control unit for acquiring information concerning the circuit pattern in an area where the defect is present based on the information concerning the position coordinate of the defect provided from the storing unit and intended to take an image thereof, calculating a restricted image taking magnification restricted based on the acquired information on the circuit pattern, determining an image taking magnification of the defect intended to take the image based on the information concerning the dimension of the defect provided from the storing unit and intended to take the image and controlling scanning means to take the defect of the image intended to take the image by the determined image taking magnification when the determined image taking magnification satisfies the calculated restricted image taking magnification; wherein the image storing unit is constituted to sample and store the digital image signal the image of which has been taken by the image taking magnification adapted to the dimension of the defect.

Further, the present invention is an automatic image sampling apparatus which is a scanning electron microscope including a storing unit for storing information concerning a kind or a classification of an appearance inspecting apparatus and a correlation with an image taking magnification; inputting means for inputting the information concerning the kind or the classification of the appearance inspecting apparatus so that a defect present on an object substrate charged into the scanning electron microscope is inspected; and a control unit for determining an image taking magnification based on the information concerning the correlation stored to the storing unit based on the information concerning the kind or the classification of the appearance inspecting apparatus inputted by the inputting means and controlling scanning means to take an image of the defect present on the object substrate by the determined image taking magnification.

Further, according to the present invention, the automatic image sampling apparatus and its method include analyzing means for calculating characteristic amounts of the defect from the digital image signal of the defect sampled and stored into the image storing unit and classifying properties of the defect by analyzing the calculated characteristic amounts.

Further, according to the present invention, information concerning a dimension of each defect is inputted from an appearance inspecting apparatus to a scanning electron microscope along with information on the position coordinate of defect and since whether position of defect can be recognized in the image of the scanning electron microscope is dependent on a relative dimension in the image of defect, the observing image magnification which is inversely proportional to the dimension of defect continuously or step by step is set and the image of the defect is taken by changing the observation magnification in accordance with the defect dimension. In inputting the image of the deject, by using defects of at least two initial points or more having large defect dimension, deviation of coordinate systems between the appearance inspecting apparatus and the scanning electron microscope is extracted and defect position information thereafter is modified. Thereby, by inputting image with an optimum magnification in accordance with the dimension of the defect, the position of the defect in the image can stably be detected and there can be realized the automatic image sampling apparatus capable of firmly inputting the image for observing the defect.

BRIEF DESCRIPTION OF THE DRAWINGS

FIGS. 14(a) and 14(b) are diagrams showing sample information and inspection information inputted to a total control unit and stored to a sample information and inspection information storing unit and control information including image taking magnification set to an image taking magnification setting unit and so on;

FIGS. 15(a) and 15(b) are diagrams showing tables in which relationships between image taking conditions and the control patterns are previously stored into a storing apparatus of the total control unit or a beam spot diameter control unit or a signal processing control unit;

FIG. 20 is a diagram showing examples of setting parameters;

DETAILED DESCRIPTION OF THE PREFERRED EMBODIMENTS

Hereinafter, embodiments of a scanning electron microscope according to the present invention will be described with reference to the drawings.

Figure 16:
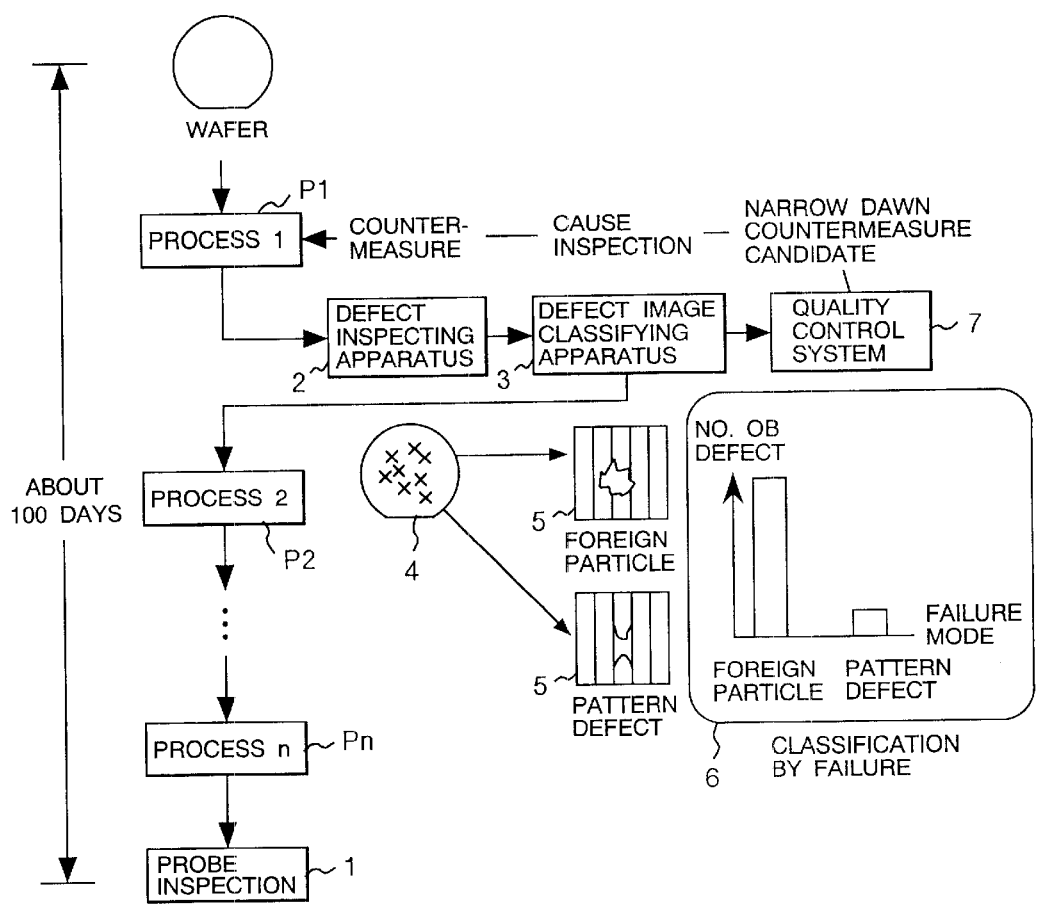
FIG. 16 is a diagram for explaining a role of an automatic image sampling apparatus by a scanning electron microscope according to the present invention in a semiconductor fabrication process.
Figure 17:
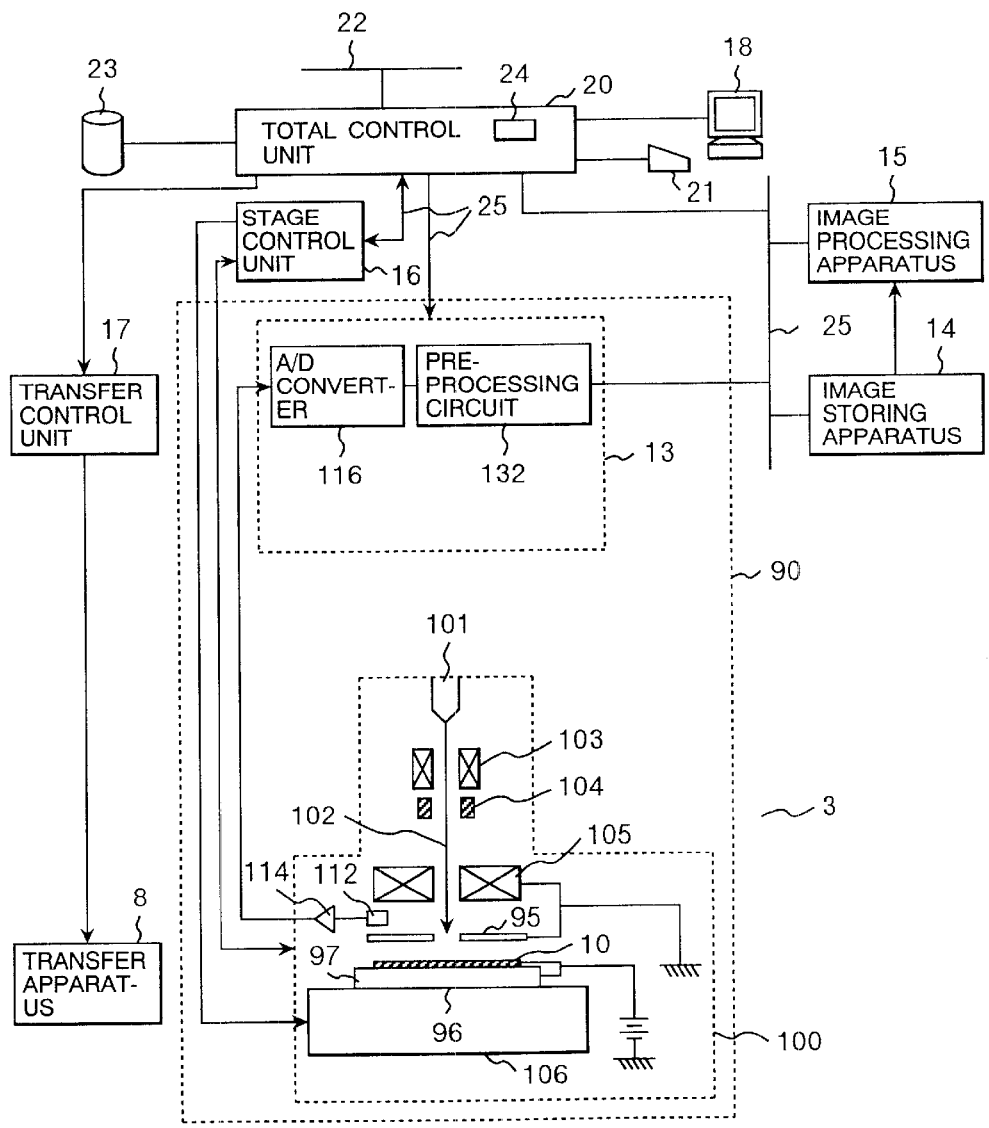
FIG. 17 is a schematic constitutional diagram showing an embodiment of an automatic image sampling apparatus by a scanning electron microscope according to the present invention.

As shown in FIG. 16, fabrication steps of a semiconductor wafer or the like according to the present invention are as many as several hundred steps and it is important in promoting the yield to discover pattern defects or adhering foreign particles (these are referred to as defects) caused in respective steps and to carry out countermeasures thereof at an early stage. Therefore, inspection of defects of pattern defects of adhering foreign particles and so on caused on a wafer (substrate) in fabrication steps is carried out by using optical appearance inspecting apparatus or optical foreign particle inspecting apparatus.

According to the optical appearance inspecting apparatus, defects of pattern defects, adhering foreign particles and the like present on a substrate such as a wafer are inspected and a number of the defects and positions thereof within the substrate are detected and accordingly, it has been difficult to estimate causes of these defects. Hence, in order to estimate causes of these defects, it is necessary to optically observe (review) these defects manually.

However, when a number of defects per each substrate. (wafer) becomes as large as one hundred through several thousands or more, it is no longer possible to review them manually as a particle of fact. Accordingly, there is needed a microscope according to the present invention for utilizing coordinates of defects detected by the inspecting apparatus and automatically taking images of defects at coordinate positions, that is, a microscope having a function of automatically sampling images of defects.

Hence, as a microscope having the function of automatically sampling images of defects according to the present invention, there is used an optical microscope or an electron beam microscope using "i" ray, ultraviolet ray (excimer laser beam) having shorter wavelength or the like capable of observing a defect having a size of several nanometers through micrometer order. Further, according to the microscope having the function of automatically sampling images of defects, it is necessary to automatically classify and determine a state of fabrication process (particularly, a state of causing a defect, that is, a category of a defect) by carrying out detailed analysis based on images of outlook defects having high resolution of an object substrate such as a semiconductor wafer or the like.

Next, description will be given of an embodiment using an electron beam microscope as a microscope having a function of automatically sampling images of defects according to the present invention with reference to FIG. 1 through FIG. 7.

Figure 1:
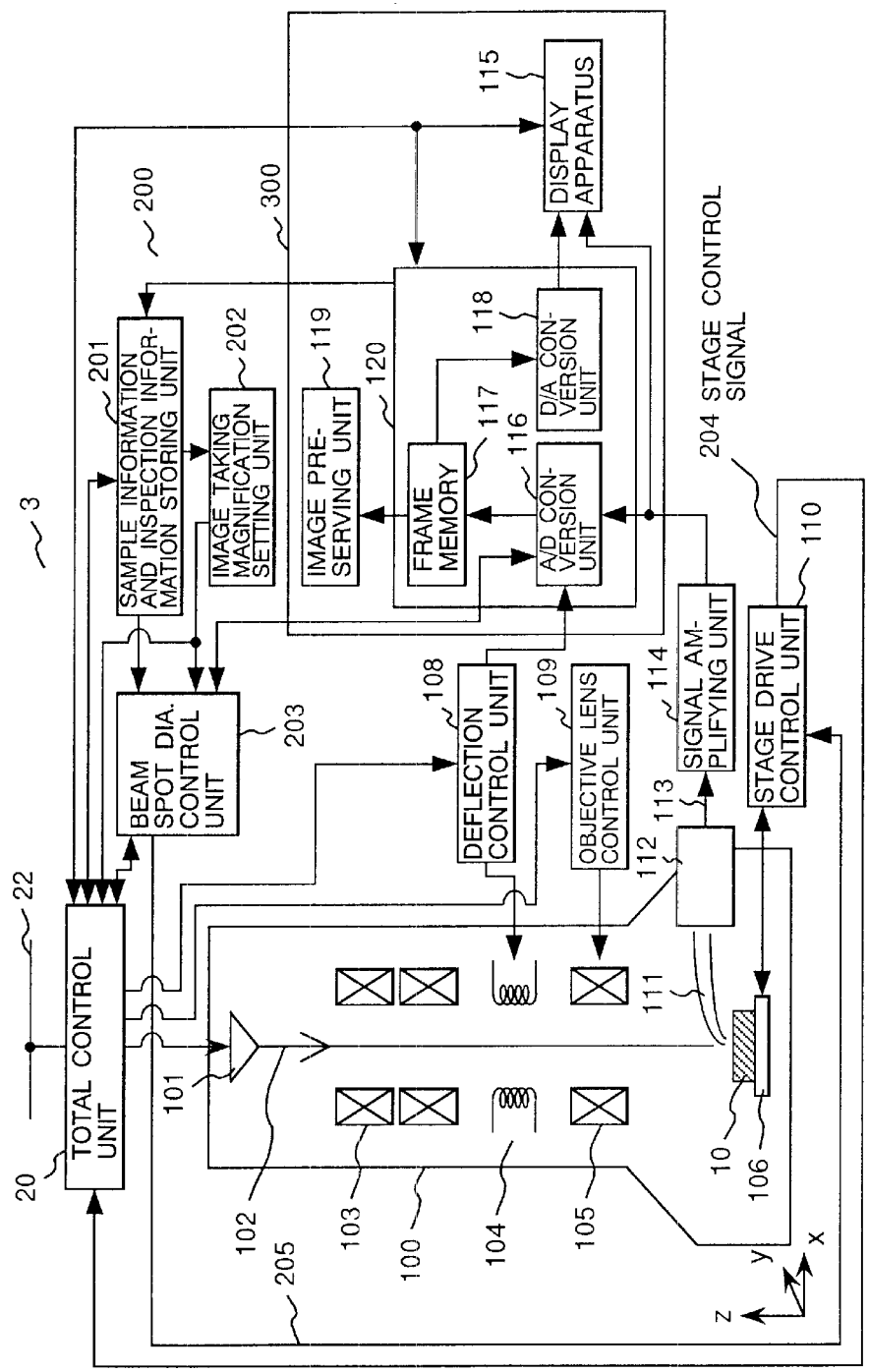
FIG. 1 is a schematic constitutional diagram showing a first embodiment of a scanning electron microscope according to the present invention.

FIG. 1 is a schematic configuration diagram showing a first embodiment of a scanning electron microscope 3 having a function of automatically sampling defect images according to the present invention.

Figure 2:
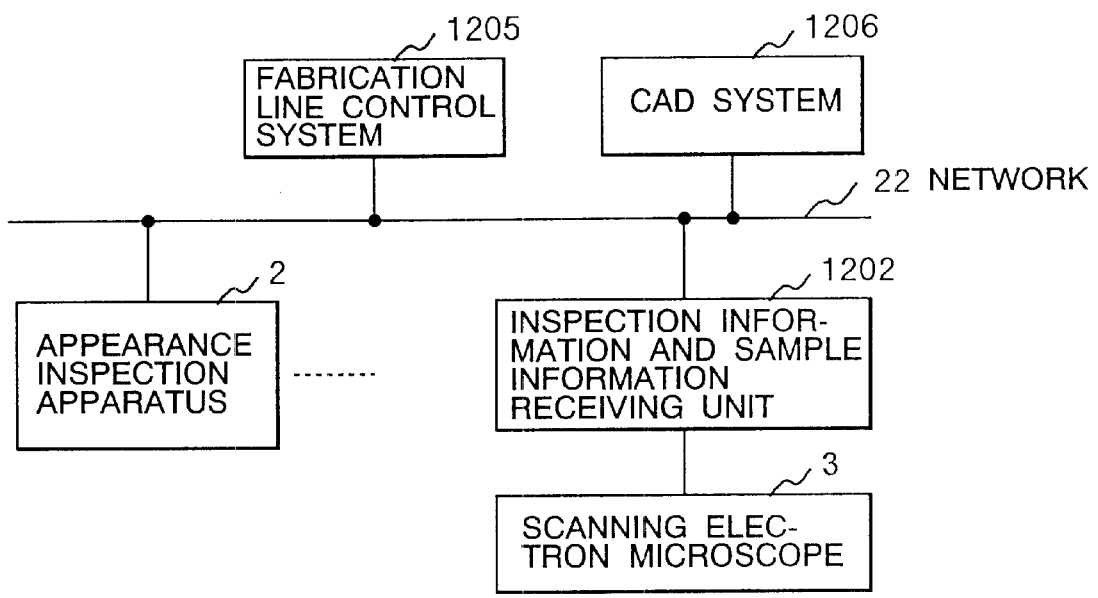
FIG. 2 is a diagram showing a schematic constitution of a total system using the scanning electron microscope according to the present invention.

To be more specific, of substrates in which defects of pattern defects, adhering foreign particles and the like have been inspected and a number of the defects and positions in the substrates has been detected by an optical appearance inspecting apparatus 2 shown by FIG. 2, an object substrate (sample) 10 for automatically classifying and determining a state of a fabrication process (particularly, a state of causing a defect, that is, a category of a defect) is charged and mounted on a stage 106. Further, in order to automatically classify and determine a state of a fabrication process (particularly, a state of causing a defect, that is, a category of a defect), previously, instruction data for instructing a category of a defect needs to form based on characteristic amounts (feature data) provided from outlook defect images (a size of a defect, a Surface texture of a defect, a gray scale value being obtained from a defect, color information on a defect and so on). Hence, an object substrate having an outlook defect for instruction is charged and mounted on the stage 106 to previously acquire an outlook defect image for instruction.

The scanning electron microscope 3 having the function of automatically sampling defect images according to the present invention is constituted by a detection optical system 100, a control system 200 and an electron beam image outputting unit 300.

The detection optical system 100 is constituted by an electron gun 101, a convergent lens 103 for converging electron beam 102 irradiated from the electron gun 101, a deflecting coil 104 for deflecting the electron beam 102, an objective lens 105 for focusing the electron beam in a spot-like shape, the stage 106 installed in a sample chamber for mounting the object substrate 10, a detector 112 for detecting secondary electron or reflected electron or absorbed electron 111 generated from the object substrate 10, and a signal amplifying unit 114 for amplifying a signal of secondary electron or reflected electron or absorbed electron detected by the detector 112.

The control system 200 is constituted by a stage drive control unit 110 for controlling the drive of the stage 106 in x-y axes directions based on a stage control signal 204 provided from the total control unit 20 and controlling the drive of the stage 106 in a z axis direction (height direction) based on a beam spot diameter control signal based on a beam spot diameter control signal provided from a beam spot diameter control unit 203, a deflection controlling unit 108 for controlling a frequency, a deflection width and so on of the electron beam deflected by the deflecting coil 104 or the like and scanning the electron beam 102 two-dimensionally on the object substrate 10 based on an instruction from the total control unit 20, an objective lens control unit 109 for controlling numerical aperture or the like of the objective lens 105 based on an instruction from the total control unit 20, a sample information and inspection information storing unit 201 for storing information in respect of the object substrate (sample) 10 inputted to the total control unit 20 and inspection information on coordinates of positions of defects or the like inspected and detected by the appearance inspecting apparatus 2, an image taking magnification setting unit 202 for setting image taking magnification of secondary electron or reflected electron or absorbed electron image of which is taken by the detector 112 in accordance with a range of two-dimensionally scanning:the electron beam 102 on the object substrate 10 based on information in respect of the object substrate (sample) stored in the sample information and inspection information storing unit 201 and an error between a coordinate system of the appearance inspecting apparatus 2 and a coordinate system of the electron microscope and so on, the beam spot diameter control unit 203 for forming a spot diameter control signal by determining a beam spot diameter on the surface of the sample which is optimum for image taking based on the image taking magnification of secondary electron or reflected electron or absorbed electron set by the image taking magnification setting unit, information in respect of the object substrate (sample) stored to the sample information and inspection information storing unit 201, information in respect of a sampling system provided from an A/D conversion unit 116, x-y-z position information of the stage 106 detected by the stage drive control unit 110 and instruction for controlling the deflection controlling unit 108 and the objective lens control unit 109 provided from the total control unit 20, and the total control unit 20.

The electron beam image outputting unit 300 is constituted by an image processing unit 120 (15) having the A/D conversion unit 116 for A/D-converting an analog signal of secondary electron or reflected electron or absorbed electron amplified and outputted by the signal amplifying unit 114 into a digital signal in synchronism with the deflection control signal provided from the deflection controlling unit 108 and providing the information in respect of the sampling system comprising period information T or the like in digital sampling to the beam spot diameter control unit 203, a frame memory 117 for temporarily storing digital electron beam image converted by the A/D conversion unit 116, an operating unit constituted by CPU or the like for subjecting image stored to the frame memory 117 to sum processing or difference processing and storing the image again to the frame memory 117 and a D/A conversion unit 118 for converting digital electron beam image stored to the frame memory 117 into analog electron beam image, a display apparatus 115 (18) for displaying the analog signal of secondary electron or reflected electron or absorbed electron amplified and outputted by the signal amplifying unit 114 and the analog electron beam image provided from the D/A conversion unit 118 and an image preserving unit 119 constituted by an optical disk, a magnetic disk, a semiconductor memory or the like for storing and preserving the digital electron beam image stored to the frame memory 117. The operating unit of the image processing unit 120 is also provided with a function of carrying out the sum processing for taking image at the same portion by plural times by the detector 112 by scanning the electron beam on the same portion by plural times and constituting the image of the portion by an average value of the plurality of images in order to promote SN ratio of the provided image and extracting difference image indicating a defect by comparing digital electron beam image having high magnification where the defect is present when digital electron beam image having high magnification is detected with digital electron image having high magnification where the defect is not present.

The sample information and inspection information storing unit 201 is provided with a function of storing information and inspection information on the sample 10 image of which is taken, which is provided by being inputted to the total control unit 20 by a keyboard, a record medium, a network or the like. The information on the sample 10 includes, for example, kind, material, color, shape, pattern, size or the like of the sample and the total control unit 20 can input and acquire from a fabrication line management system (a field management system) 1205 managing a fabrication line for fabricating the sample (object substrate), from a CAD system 1206 having design information via a network 22 or a record medium shown by FIG. 2. In respect of pattern of the sample, there is included information on presence or absence of a pattern formed on the surface of the sample, presence or absence of periodicity of the pattern, a period of the periodic pattern and the like. Further, when the sample 10 is provided with pattern or color which differs by respective fabrication steps as in a semiconductor wafer, names of the fabrication steps can be included as information provided from the fabrication line management system 1205. Other than these, when position information on an image taking portion in the sample 10 is previously determined, the position information is also included. The sample information may be a design value previously determined in respect of the sample or other value of coordinates of a position of a defect detected by the outlook detecting apparatus 2. Further, the sample information may be a value sampled by adding an arbitrary processing to analog data or digital data acquired at the image processing unit 120. For example, the value may include frequency components of a detected signal provided from the image processing unit 120 by subjecting provided digital data to Fourier Transformation processing.

At the image taking magnification setting unit 202, magnification of taking image of the sample 10 is set. The magnification may be a value provided from outside of the scanning electron microscope according to the present invention to the image taking magnification setting unit 202 or may be a value provided based on information concerning the sample stored to the sample information storing unit 201. The image taking magnification is set to high magnification for acquiring digital image having high resolution for analyzing in details, for example, a defect portion (when the magnification is, for example, about 10,000 or more, for example, 30,000 through 60,000, the field of view becomes about 1 through 2 $\mu$m and a defect of 0.1 $\mu$m can be recognized by a size of about 3 mm through 6 mm) and low magnification capable of specifying the position of the defect portion (when the magnification is about 10,000 or low, for example, 10,000, the field of view becomes about several through 10 $\mu$m and can be made to fall within an error between coordinate systems in various kinds of outlook inspection apparatus and a coordinate system in the electron beam microscope, and further, a defect of 0.1 $\mu$m can be recognized with a size of about 1 mm).

The beam spot diameter control unit 203 is provided with a function of determining a beam spot diameter on the surface of the sample which is optimum in taking image, based on information concerning sampling within the sample information and inspection information storing unit 201, the image taking magnification setting unit 202 and the A/D conversion unit 116. The information in respect of sampling provided from the A/D conversion unit 116 includes period information in digital sampling or the like. Further, although an explanation has been given such that the sampling period T is made constant when image is taken at low magnification and when image is taken at high magnification in sampling and quantizing at the A/D conversion unit 116, the sampling period T may be changed depending on the case of taking image at low magnification and the case of taking image at high magnification. When the sampling period T is changed at the A/D conversion unit 116, the sampling period may be changed based on a beam spot diameter control signal outputted from the beam spot diameter control unit 203.

Next, description will be given of automatically sampling image by using the scanning electron microscope 3 as a microscope based on coordinates of defects in the object substrate inputted and provided from the optical appearance inspecting apparatus 2 to the total control unit 20 by a network or a record medium with reference to FIG. 3.

First, in step S301, an aggregation of coordinates of a number of defect portions inspected and detected by the optical outlook inspection apparatus 2 with regard to a plurality of the object substrates 10 charged into the scanning electron microscope 3, is inputted to the total control unit 20 by the network 22 or a record medium of a disk or the like and is stored to the sample information and inspection information storing unit 201.

Next, in step S302, the total control unit 20 reads a coordinate of a position of one defect portion in defect portions on the object substrate 10 charged and mounted onto the stage 106 by selecting it from the sample information and inspection information storing unit 201.

Next, in step S303, the total control unit 20 positions the position of the selected defect portion substantially on an optical axis of the electron beam 102 by moving the stage 106 based on instruction outputted to the stage drive control unit 110 for taking electron beam image at the selected. coordinate portion on the object substrate 10.

Figure 6A:
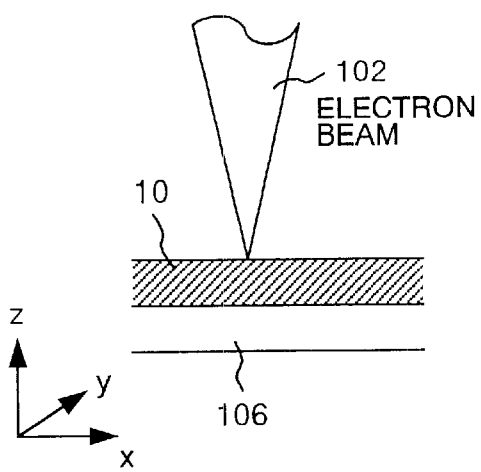
FIGS. 6(a) and 6(b) are views showing beam spot diameters in a focused state of electron beam controlled to switch onto a sample (object substrate)
Figure 6B:
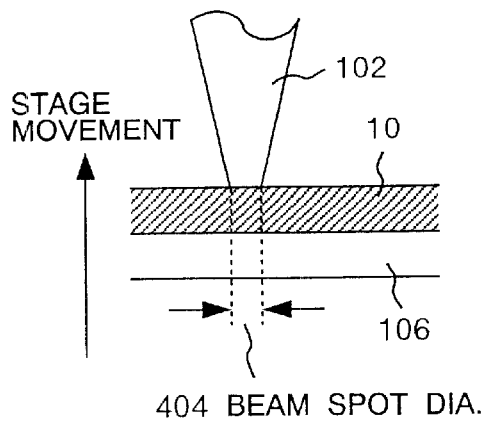

Next, in step S304, after moving and positioning the stage 106, the total control unit 20 enlarges a two-dimensional scan width of the electron beam 102 on the object substrate 10 of the electron beam 102 to about several through 10 μm by controlling the deflection controlling unit 108 such that electron beam image having low magnification set by the image taking magnification setting unit 202 can be taken by the detector 112. At the same time, in order to prevent high frequency noise components from being included in electron beam image detected by the detector 112 in correspondence with the low magnification set by the image taking magnification setting unit 202, the beam spot diameter control unit 203 provides the beam spot diameter control signal to the stage drive control unit 110 to thereby lift the stage 106 in z direction so that as shown in FIG. 6(b), the electron beam 102 is irradiated to the defect portion on the object substrate 10 in a defocused state by enlarging the beam spot diameter as indicated by numeral 404, electron beam image which does not include noise components is taken by the detector 112 by the low magnification at the defect portion, converted into digital electron beam image by the A/D conversion unit 116 and is stored to the frame memory 117. The low magnification, mentioned here, is set as image taking magnification of up to about 10,000 such that the defect portion is positioned in the field of view (about several through 10 μm) in accordance with the error between coordinate systems in the outlook inspection apparatus 2 of various kinds and the coordinate system in the electron microscope 3. In this way, when the low magnification is set to about 10,000, the field of view becomes about several through 10 μm and a defect of 0.1 μm can be recognized by a size of about 1 mm.

Next, in step S305, the total control unit 20 instructs the stage drive control unit 110 to move the stage 106 to thereby position a portion with no defect having a background being the same as that of the defect portion at the optical axis of the electron beam 102 based on sample information stored to the sample information and inspection information storing unit 201. Further, the electron beam 102 is irradiated to the no defect portion in the defocused state with the two-dimensional scan width (low magnification) being the same as that in step S304, electron image having no noise component is taken at the no defect portion by low magnification by the detector 112, converted into digital electron beam image by the A/D conversion unit 116 and is stored to the frame memory 117. For example, for a semiconductor product, a plurality of chips having the same structure are arranged on a wafer thereof and a pattern thereof is formed and accordingly, for example, the above-described operation is carried out by taking electron beam image at the same portion of a contiguous chip. When electron beam image at a portion with no defect having a background being the same as that of the defect portion can previously be acquired and can be stored to a storing apparatus such as memory or the like (for example, 119) installed at inside or outside of the microscope, the step S305 can be omitted.

Next, in step S306, the image processing unit 120 extracts difference image by positioning two of the electron beam images taken in step S304 and step S305 and having no noise components relative to each other and a portion producing a difference in the extracted difference image can be recognized as a defect portion. For example, the defect portion can be recognized by displaying the extracted difference image on the display apparatus 115 and by feeding back the coordinate of the recognized defect portion to the total control unit 20, the total control unit 20 can accurately position the defect portion which is recognized by being taken at the low magnification to the optical axis of the electron beam 102. Further, recognition of the coordinate of the defect portion by the low magnification may be executed by the operating unit in the image processing unit 120. Further, by designating the defect portion by the low magnification displayed at the display apparatus 115 on the screen, the position coordinate can be outputted form the display apparatus 115 and provided to the total control unit 20.

Next, in step S307, the total control unit 20 positions the defect portion to the optical axis of the electron beam 102 accurately with an accuracy of about 1 μm or lower by moving the stage 106 by controlling the stage drive control unit 110 based on the position coordinate of the defect portion which is recognized based on electron beam image having the low magnification provided from the image processing unit 120 or the display apparatus 115. Further, the total control unit 20 narrows the two-dimensional scan width of the electron beam 102 on the object substrate 10 of the electron beam 102 to about 1 through 2 μm or lower by controlling the deflection controlling unit 108 such that electron beam image having high magnification of, for example, about 30,000 through 60,000 set by the image taking magnification setting unit 202 can be taken by the detector 112. At the same time, in order to be able to take ultra fine electron beam image having high resolution capable of honestly calculating characteristic amounts of the defect in correspondence with high magnification set by the image taking magnification setting unit 202, the beam spot diameter control unit 203 provides the beam spot diameter control signal to the stage drive control unit 110 to thereby lower the stage 106 in the z direction so that as shown in FIG. 6(a), the electron beam 102 is irradiated to the defect portion of the object substrate 10 in a focused state, ultra fine electron beam image having high resolution is taken with high magnification at the defect portion by the detector 112, converted into digital electron beam image by the A/D conversion unit 116 and stored to the frame memory 117. The high magnification, mentioned here, is image taking magnification of 10,000 or more (for example, about 30,000 through 60,000) capable of providing digital electron beam image having high resolution. When the image taking magnification is set to high magnification of, for example, 30,000 through 60,000, a defect of 0.1 $\mu$m can be recognized by a size of about 3 mm through 6 mm and a defect of 0.05 $\mu$m can be recognized by a size of about 1.5 mm through 3 mm, digital electron beam image having high resolution can be acquired and detailed analysis can be carried out by extracting characteristic amounts (size, shape, surface texture, gray scale value and so on) of the defect portion based on the acquired digital electron beam image having high resolution.

In this way, the defect portion inspected and detected by the appearance inspecting apparatus 2 is positioned in the coordinate system of the electron microscope and accordingly, the defect portion can be positioned within a field of view having high magnification of 10,000 or more. As a result, ultra fine electron beam image having high resolution can be taken with high magnification including the defect portion. Further, since ultra fine electron beam image having high resolution can be taken with high magnification including the defect portion, characteristic amounts (size, shape, surface texture, gray scale value and so on) of the defect can be extracted based on the ultra fine defect electron beam image having high magnification and based on the characteristic amounts and previously instructed instruction data (a relationship between a representative characteristic amount of defect and category of the defect), the category of the defect (a kind capable of presuming cause of generating defect) can be classified.

Next, in step S308, the total control unit 20 confirms whether or not electron beam image has finished to be taken in respect of all of defect portions based on inspection information inspected by the appearance inspecting apparatus 2 and stored to the sample information and inspection information storing unit 201. When there remain data to be taken, the operation returns to step S302 and when all of the data has been taken, automatic sampling of image is finished.

According to automatic sampling of image, as described above, in step S304, firstly, image of defect portion is taken by low magnification, and position of the defect portion is sampled by the coordinate system of the electron microscope. Then, in step S307, image of the portion is taken with high magnification. Originally, the object of acquiring ultra fine electron beam image of defect portion is achieved only by taking the image with high magnification at the electron microscope based on position of the defect coordinate provided by the appearance inspecting apparatus. The reason of taking the image with high magnification after once taking the image with low magnification here is that there is an error between the coordinate provided by the appearance inspecting apparatus 2 and the coordinate used in the electron microscope 3 for determining movement of the stage 106 and the field of view for taking the image and accordingly, even when image of the coordinate position of defect from the appearance inspecting apparatus 2 is intended to take with high magnification, there is no guarantee that the defect portion is brought into the field of view. Accordingly, in consideration of the error between the coordinate system of the appearance inspecting apparatus 2 and the coordinate system of the electron microscope 3, based on inspection information stored to the sample information and inspection information storing unit 201, the image taking magnification with low magnification at the electron microscope 3 is determined and set by the image taking magnification setting unit 202. As a result, when the object substrate 10 having the defect portion is charged and mounted onto the stage 106 of the electron microscope 3, the defect portion can be positioned in the field of view for taking the image with low magnification (about several through 10 $\mu$m).

Further, the reason of calculating the difference image between the electron beam image which does not include noise components by the low magnification at the defect portion and the electron beam image which does not include noise components by the low magnification at the portion with no defect having the background being the same that in the defect portion by the image processing unit 120 at the step S306, is that by carrying out the difference image calculation of the two images at portions having the same background, the difference portion can easily be recognized as the defect portion and the position of the defect portion can be specified by sampling the position in the coordinate system of the electron microscope.

In step S306, the difference image calculation carried out by the image processing unit 120 is executed by using two-dimensional digital images provided by converting the electron beam images detected by the detector 112 in analog-to-digital conversion by the A/D conversion unit 116. When an analog signal is converted into a digital signal at the A/D conversion unit 116, if a frequency component w of the analog signal and the sampling interval T in digital sampling do not satisfy a sampling principle shown by Equation (1), as described below, an analog image signal including information on a defect portion detected by taking image thereof at low magnification, cannot be converted into a digital image signal accurately without causing pseudo noise components. The reason is that generally, pseudo noise referred to as moire is caused in digital data converted under a condition which does not satisfy the sampling principle. Therefore, when the difference image processing is carried out in step S306 in a state of including such a noise, there is a high possibility of erroneously recognizing a portion of producing a difference in the electron beam image caused by noise as a defect portion. As a result, there is a case in which the defect portion cannot be specified by the electron beam coordinate system and electron beam image with high magnification of the defect portion cannot accurately be acquired in step S307.

In this case, the sampling principle is a principle in which when the frequency component included in the analog signal component before digital conversion is designated by notation. w and the sampling interval in sampling the analog signal component is designated by notation T, the condition of Equation (1) shown below needs to satisfy. This is a, relationship between ① the frequency component w of the detected analog signal and ② the digital sampling interval T.

$$T < \tfrac{1}{2} w \qquad (1)$$

In the case of taking image of defect caused in fabrication steps of a semiconductor or the like by a scanning electron microscope, what are related to ① the frequency component of the detected analog signal are a frequency component provided by an object to be observed (object substrate 10), that is, a pattern per se of a semiconductor wafer and a beam diameter when a surface thereof is detected by electron beam.

According to the scanning electron microscope 3, when an electron beam diameter on the surface of the sample 10 is provided with a size of a degree being the same as fine irregularities of the pattern, an analog signal detected by the detector 112 is superposed with a frequency component of a degree being the same as that of the irregularities of the surface. However, when the beam diameter at the surface of the sample 10 is sufficiently larger than the irregularities of the pattern, the detected analog signal is not superposed with the frequency component of a degree being the same as that of the fine irregularities of the pattern. Thereby, when electron beam image is taken by the detector 112 by a control in which the electron beam diameter at the surface of the sample 10 is much larger than the. frequency component provided to the pattern of the surface of the sample of the object of taking image, that is, by defocusing (dimming) the image as shown in FIG. 6(*b*) based on the beam spot diameter control signal from the beam spot diameter control unit 203, the frequency component of the detected analog signal is provided with only a component which is much lower than the frequency component provided to the pattern of the surface of the sample and the image can be taken under the condition satisfying Equation (1). Therefore, the portion of defect detected by the coordinate system of the appearance inspecting apparatus 2 can be positioned in the field of view for taking image with low magnification in the electron microscope 3 and the position of the defect portion can be recognized and specified in the coordinate system of the electron microscope 3.

Figure 4A:
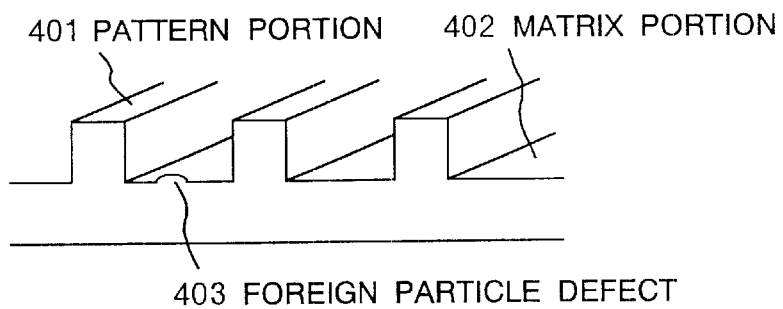
FIG. 4(a) is a view showing a pattern formed on a sample and a foreign particle defect present on the sample.
Figure 4B:
FIGS. 4(b) and 4(c) are diagrams showing analog signal waveforms of electron beam detected by a focused state of electron beam with which irradiates the sample shown in FIG. 4(a)
Figure 4C:
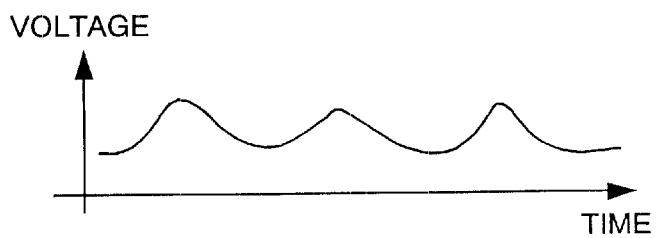

However, when a degree of defocusing is excessively large, the signal component of the defect portion to be sampled is not detected by the detector 112. FIGS. 4(*a*), 4(*b*) and 4(*c*) are diagrams schematically explaining this state. FIG. 4(*a*) is a sectional view showing an embodiment of the surface of a sample to be detected. FIGS. 4(*b*) and 4(*c*) show waveforms of analog signals respectively detected from the same portion. To be more specific, FIG. 4(*b*) shows a waveform of an analog signal detected by taking the electron beam diameter on the surface of the sample to be substantially the same as the size of irregularities of the surface and FIG. 4(*c*) shows a waveform of an analog signal detected by controlling the electron beam diameter on the surface of the sample much larger than the size of the irregularities of the surface. FIG. 4(*a*) shows the sample 10 in which a pattern portion 401 is formed above a matrix portion 402 and a defect 403 of a foreign particle or the like adheres onto the matrix portion 402. When the waveform shown by FIG. 4(*b*) is viewed, a mountain of a waveform caused by detecting the defect 403 of a foreign particle or the like is observed. Further, a voltage value of a portion in correspondence with an edge portion of the pattern 401 becomes higher than a voltage value at the surrounding since an edge defect particularly to a detected waveform of a scanning electron microscope is manifested. In a state of excessive defocusing as shown in FIG. 4(*c*), a frequency component in correspondence with a frequency component of fine irregularities of the pattern 401 is not superposed on the detected signal. As a result, it is known that the defect portion 403 of a foreign particle or the like cannot be observed in accordance with a deterioration in the waveform of the signal component. Even when the analog signal detected by the detector 112 under such a state is converted into a digital signal by the A/D conversion unit 116, it is difficult to detect the defect by digital signal processing at the image processing unit 120. The size of a defect to be detected is normally ½ through ⅓ of a minimum dimension of a pattern formed on the semiconductor product and about 0.2 through 0.05 μm. Hence, in order to determine the beam spot diameter in a defocused state necessary for detecting a defect to constitute a target under a state in which the sampling principle is satisfied in the beam spot diameter control unit 203, a consideration needs to be given also to sample information on a size of a pattern, a period of pattern or the like stored to the sample information and inspection information storing unit 201.

Next, description will be given of ② digital sampling interval sampled and quantized at the A/D conversion unit 116.

To be more specific, in the A/D conversion unit 116, it is determined in what number of digital data of one scan portion of beam scanning based on control of the deflection controlling unit 108 in respect of the deflecting coil 104 is sampled. This is determined as the apparatus specification of the electron microscope. This is determined as apparatus specification of the electron microscope. For example, when sampling is carried out by 512 times, a number of pixels in the scanning direction of the provided digital image becomes 512 pixels. Meanwhile, a scanning width controlled by the deflection controlling unit 108 based on instruction of the total control unit 20 is determined by magnification of image set by the image taking magnification setting unit 202. In the case of low magnification, compared with the case of high magnification, a relatively large area (about several through 10 μm) is scanned at a time, and therefore, even when a number of sampling times stays constant, an interval between sampled data on the object substrate is widened. To be more specific, with regard to ② digital sampling interval, the image taking magnification becomes an important item thereof. At any rate, the image taking magnification at low magnification is determined to about 10,000 or smaller (about several through 10 μm) at the image taking magnification setting unit 202 by being inputted to the total control unit 20 in accordance with the error between the coordinate systems of various kinds of the appearance inspecting apparatus 2 and the coordinate system in the electron microscope 3. To be more specific, since the object substrate 10 having defect portions inspected and detected by various kinds of the outlook inspection apparatus 2 is charged into the electron microscope, the image taking magnification of low magnification in the electron microscope 3 is determined such that defect portions are disposed within the field of view of low magnification when they are positioned in the coordinate system of the electron microscope based on the coordinate data of the defect portions in the object substrate 10 inspected and detected by various kinds of the outlook inspection apparatus. Therefore, when images of defect portions in the object substrate 10 charged and mounted onto the stage 106 of the electron microscope, is taken at low magnification, it becomes possible to acquire digital image signals indicating the defect portions and to specify position coordinates of the defect portions by the coordinate system of the electron microscope and it becomes possible to dispose the defect portions within the field of view with high magnification, acquire digital image signals with high resolution by high magnification and analyze in details in respect of the defect portions.

Figure 3:
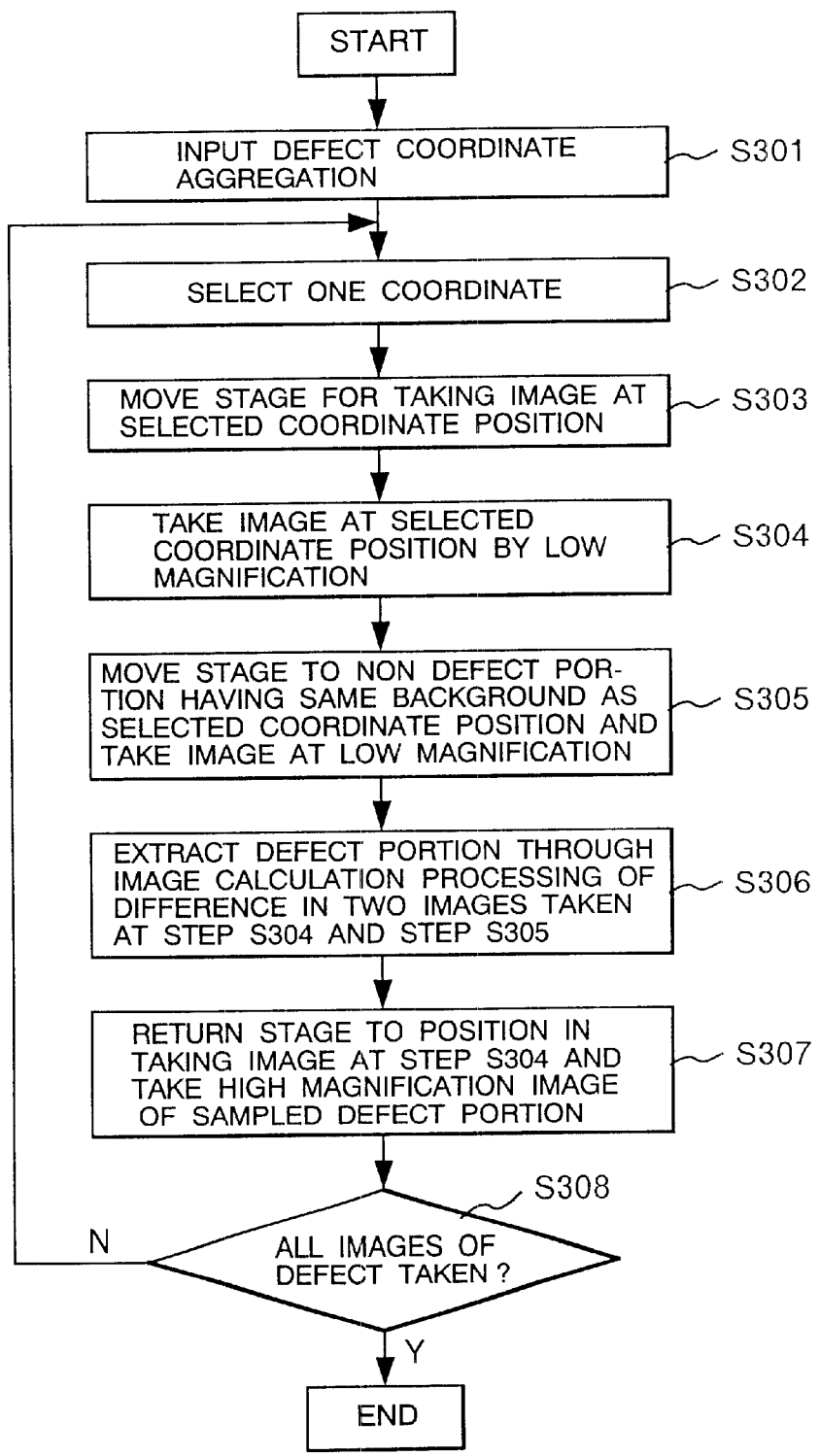
FIG. 3 is a diagram showing a processing flow of sampling image by using the scanning electron microscope according to the present invention.

In automatic sampling of image shown by FIG. 3, in step S304 and step S307, image of the same portion is taken by different magnifications by the electron microscope. Further, for the object. substrate 10, different patterns are formed for respective products and accordingly, period of pattern and size of pattern also differ. Accordingly, in the electron microscope, to accurately carry out A/D conversion and extract defect areas, the operation must be controlled such that the following three items satisfy the sampling principle by Equation (1).

(1) A frequency component provided to a surface pattern of the object substrate, (2) An electron beam diameter on a surface of the object substrate in taking image, and (3) Image taking magnification.

In this way, the beam spot diameter control unit 203 determines (1) the frequency component provided to the surface pattern of the object substrate which is provided from the sample information and inspection information storing unit 201, (3) image focusing magnification (particularly, low magnification) set by the image taking magnification setting unit 202, and (2) the electron beam diameter on the surface of the object substrate particularly when image is taken at low magnification based on the sampling interval at the A/D conversion unit 116. Based on the determined beam spot diameter control signal 205, the stage drive control unit 110 is controlled and electron beam is irradiated to the surface of the object substrate in a defocused state, so that digital image showing defect portions taken with low magnification can be acquired without causing noise components by satisfying the sampling principle of Equation (1).

Next, description will be given further to a method of taking electron beam image of the object substrate (sample) 10 without causing noise components.

Figure 5A:
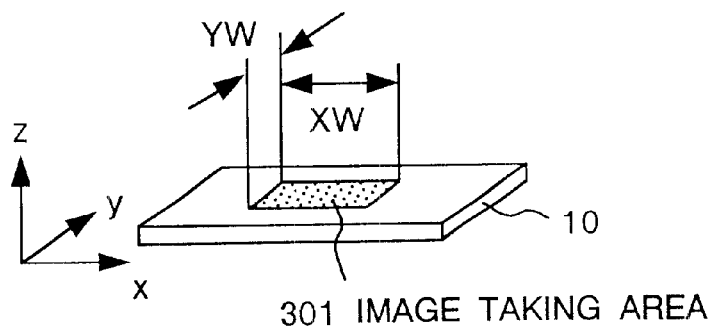
FIG. 5(a) is a view showing an image taking area by electron beam.
Figure 5B:
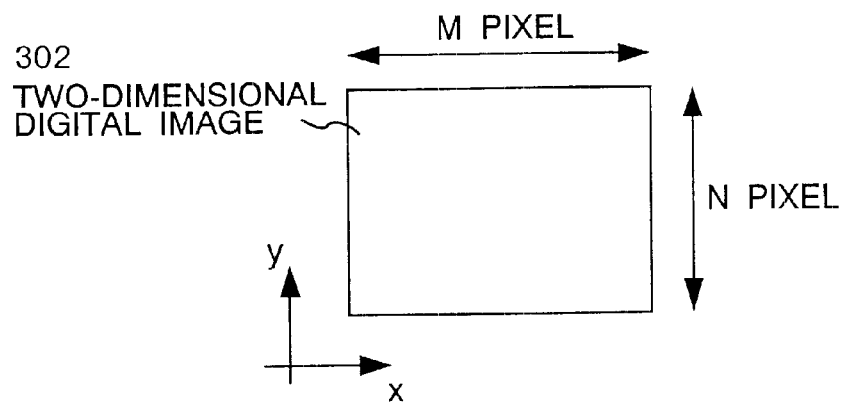
FIG. 5(b) is a view showing tow-dimensional digital image taken from the image taking area shown in FIG. 5(a)

FIG. 5(a) shows an image taking area 301 taken when an image of the sample 10 is taken by the scanning electron microscope and FIG. 5(b) shows two-dimensional digital image 302 of the image taking area 301. Area sizes xw and yw in x and y directions of the image taking area 301 indicate a size of an area on which the electron beam 102 is made to scan on the sample 10 by the deflection coil 104. Assume that the two-dimensional digital image 302 provided from the A/D conversion unit 116 is constituted by M and N pixels respectively in x and y directions. In providing the two-dimensional digital image 302 in respect of the image taking area 301, in view of x direction, a one-dimensional analog electric signal provided by one scan of electron beam 102 over the distance xw, is digitally sampled into M of digital data and in respect of y direction, N times of scanning of the electron beam 102 over the distance xw are carried out in respect of the distance yw in y direction.

This signifies that analog electric signals detected from the sample 10 are sampled as data of N and M respectively in x and y directions with regard to both of x and y directions and in this case, to accurately take the two-dimensional digital signal 302, the sampling principle (Equation (1)) needs to satisfy between a frequency component of the analog digital signal produced by converting an intensity distribution of secondary electron emitted from the sample 10 and the sampling interval. When digital sampling is carried out under a condition which does not satisfy the sampling principle, two-dimensional digital image includes noise.

When pixel numbers (M, N) to be sampled stay constant regardless of the image taking magnification, in the case in which scan. areas xw and yw are large, that is, the image taking magnification is large, compared with the case in which the scan areas xw and yw are small, that is, the image taking magnification is small, a spacial period of digital sampling becomes large. This signifies that the control must be carried out such that the sampling principle is established between the frequency component of the analog electric signal of the secondary electron intensity distribution and the sampling interval in accordance with a change in the image taking magnification. The control is grossly classified into two methods of (A) secondary electron is detected such that components having frequencies equal to or larger than a frequency provided by the sampling principle are not included in the detected analog electric signal and (B) components having frequencies higher than the frequency provided by the sampling principle are removed from the detected analog electric signal. Description will be given later of the method of (B) with reference to FIG. 10 and at this occasion, description will be given of the method of (A).

FIGS. 6(a) and 6(b) show a behavior of irradiating the sample 10 with the electron beam. In FIG. 6(a), the electron beam 102 is converged substantially in a dot-like shape on the sample 10. A secondary electron intensity distribution detected in such a beam shape, includes high frequency components in correspondence with a fine shape on the sample or the like. In the meantime, FIG. 6(b) shows the state in which the stage 106 is moved in z direction from the state of FIG. 6(a). In this case, the electron beam 102 is not sufficiently converged onto the surface of the sample and a beam spot diameter 404 on the sample is provided with a value larger than that in the case of FIG. 6(a). When image is taken under the state, an analog electric signal of a detected two-dimensional electron intensity distribution does not include high frequency components in correspondence with a fine shape of a surface of the sample or the like and the taken image becomes a defocused (dimmed) image. In this way, by taking image in the defocused state by controlling the beam spot diameter of the electron beam on the sample, high frequency components of the acquired secondary electron signal intensity distribution can be eliminated. To be more specific, by controlling the beam spot diameter to an arbitrary size, components of frequencies higher than an arbitrary frequency can be prevented from being included in an analog electric signal produced by converting detected secondary electron.

Figure 7:
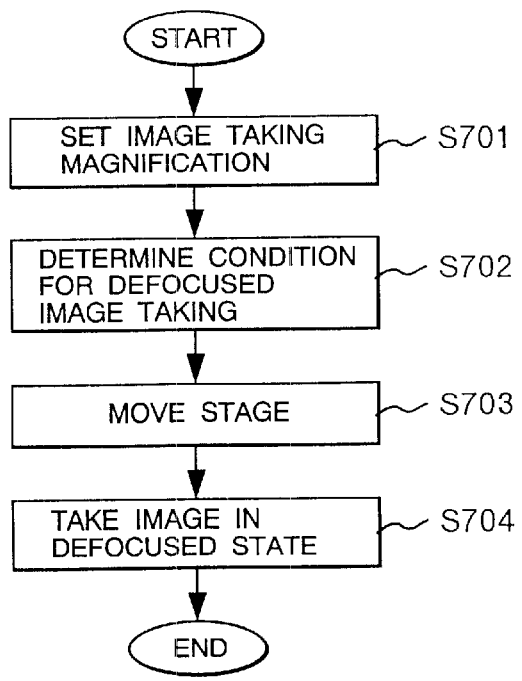
FIG. 7 is a diagram showing a control flow for controlling electron beam to take image in a defocused state onto a sample (object substrate)

FIG. 7 shows a sequence of taking image without causing noise by using the above-described principle according to the embodiment of the present invention shown in FIG. 1. First, in step S701, image taking magnification is set to the image taking magnification setting unit 202. As mentioned above, the set value may be calculated from content of the sample information and inspection information storing unit 201 or may be inputted directly from outside by the user. Next, in step S702, the beam spot diameter control unit 203 determines conditions of taking defocused image to satisfy the sampling principle by using the image taking magnification set by the image taking magnification setting unit 202 and information with regard to the sampling system provided from the A/D conversion unit 116. The conditions include a value of the beam spot diameter on the surface of the sample and a moving amount of the stage 106 for taking image with the beam spot diameter. Next, in step S703, the stage 106 is moved in z direction based on control by the stage drive control unit 110 by using the beam spot diameter control signal such that image is taken by the determined conditions. Further, in step S704, the total control unit 20 controls the deflection controlling unit 108 to thereby control the deflection coil 104 in accordance with the image taking magnification set by the image taking magnification setting unit 202, so that the electron beam 102 is irradiated to a two-dimensional scanning range on the surface of the sample 10 and electron beam image is taken by the detector 112 with the image taking magnification.

When a periodic pattern is formed on the sample 10 constituting the object of image taking, an analog electric signal detected by the detector 112 may be superposed with frequency components caused by the frequency of the pattern on the sample depending on the image taking magnification and therefore, the beam spot diameter control unit 203 can determine image taking conditions for satisfying the sampling principle in respect of various patterns of samples by using information in respect of the pattern of the image taking object stored to the sample information and inspection information storing unit 201, information on image taking magnification set by the image taking magnification setting unit 202 and the sampling interval provided from the A/D conversion unit 116. To be more specific, even when image of any object is taken by any magnification, the beam spot diameter control unit 203 can accurately take the image without causing pseudo noise by controlling the beam spot diameter to satisfy the sampling principle.

Figure 8:
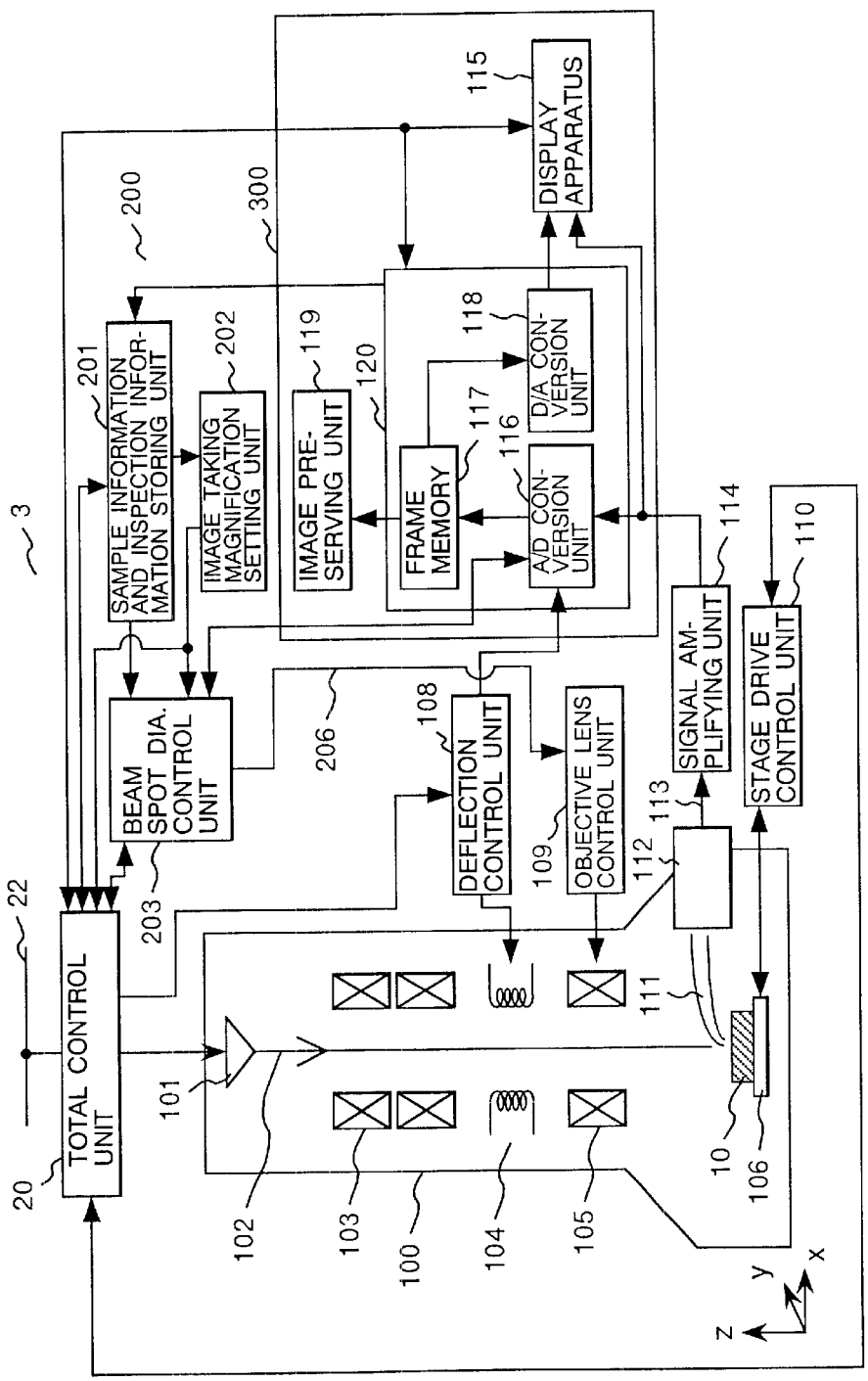
FIG. 8 is a schematic constitutional diagram showing a second embodiment of a scanning electron microscope according to the present invention.

Next, description will be given of a second embodiment of a scanning electron microscope for automatically sampling defect image according to the present invention with reference to FIG. 8. According to the second embodiment, as a method of controlling the spot diameter of the electron beam 102 on the sample 10, there is used a method in which a characteristic of the objective lens 105 used for converging the electron beam 102 on the sample 10 is changed without moving the stage 106 in the z direction as shown by the first embodiment in FIG. 1. Other constitution of the second embodiment is the same as that of the first embodiment shown in FIG. 1. To be more specific, the beam spot diameter control unit 203 determines image taking conditions satisfying the sampling principle and instructs: the objective lens control unit 109 to change (control) the numerical aperture of the objective lens 105 by using an objective lens control signal 206 to take image under such a condition. By changing the numerical aperture of the objective lens 109, as shown in FIG. 6(*b*), the electron beam spot diameter 404 on the surface of the sample 106 can be enlarged and electron beam image can be taken under the defocused state as shown in FIG. 6(*b*).

Figure 9:
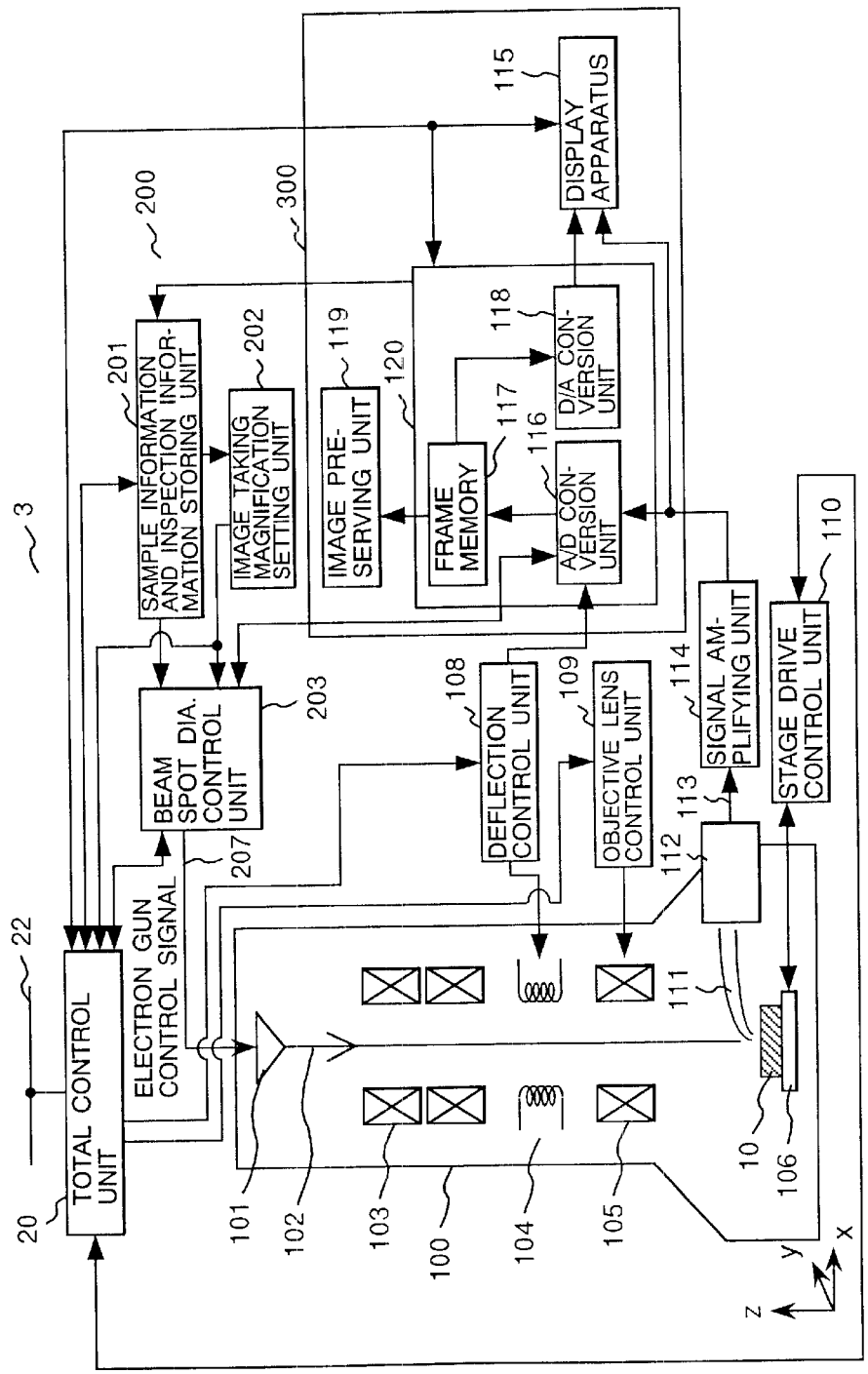
FIG. 9 is a schematic constitutional diagram showing a third embodiment of a scanning electron microscope according to the present invention.

Next, description will be given of a third embodiment of a scanning electron microscope for automatically sampling defect image according to the present invention with reference to FIG. 9. The third embodiment is of a system of controlling beam current of the electron beam 102 emitted from the electron gun 101 to take an image of the sample 10 in the defocused state. Other constitution of the third embodiment is the same as that in the first embodiment shown in FIG. 1.

When beam diameter of the electron beam 102 is designated by notation d and beam current is designated by notation i, the following relationship of Equation (2) is established. Equation (2) shows a relationship in which by increasing the beam current of the electron beam 102, the electron beam spot diameter on the surface of the sample 10 is also increased.

$$d = K \times i \quad (2)$$

where notation K designates a constant.

To be more specific, the beam spot diameter control unit 203 can enlarge the electron beam spot diameter 404 on the surface of the sample 10 as shown in FIG. 6(*b*) by increasing the beam current emitted from the electron gun 101 on the basis of an electron gun control signal 207 to thereby enable to take electron beam image in the defocused state. Further, by increasing the beam current in this way, there can be achieved an advantage of capable of accelerating beam scanning.

Figure 10:
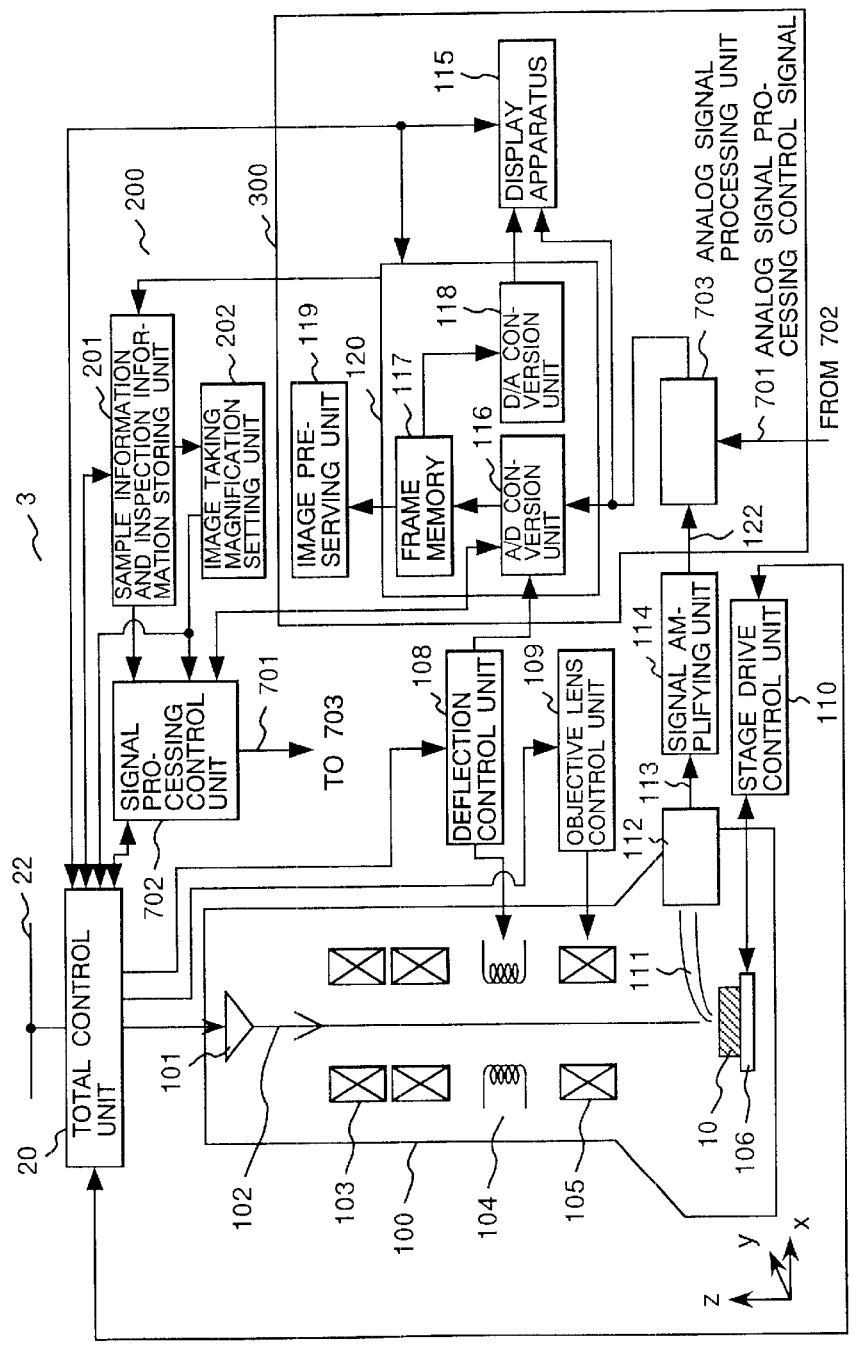
FIG. 10 is a schematic constitutional showing a fourth embodiment of a scanning electron microscope according to the present invention.
Figure 11:
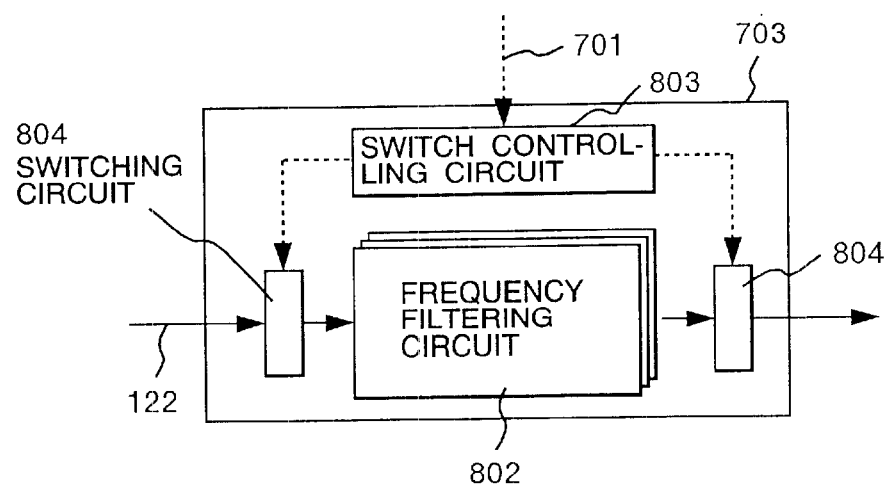
FIG. 11 is a diagram showing an embodiment of a specific constitution of an analog signal processing unit shown in FIG. 10.

Next, description will be given of a fourth embodiment of a scanning electron microscope for automatically sampling defect image according to the present invention with reference to FIG. 10. According to the first, the second and the third embodiments, upon taking image by low magnification, the electron beam 102 is defocused on the sample 10, so that a detected analog electric signal of an intensity distribution of secondary electron is controlled not to include frequency components equal to or higher than a constant frequency, with a result that a digital image signal having low magnification indicating a true defect portion which does not include noise components is provided from the A/D conversion unit 116 to thereby specify the position of the defect portion within the field of scope of low magnification. In the meantime, according to the fourth embodiment shown in FIG. 10, in an analog signal processing unit 703, by removing frequency components of a predetermined frequency or higher from the detected analog electric signal 113, a digital image signal of low magnification showing the true defect portion which does not include noise components is provided from the A/D conversion unit 116 to thereby specify the position of the defect portion within the field of view of low magnification. The fourth embodiment includes a signal processing control unit 702 for determining content of processing with regard to a detected signal and the analog signal processing unit 703 for carrying out analog signal processing based on information concerning the sample information and inspection information storing unit 201, the image taking magnification setting unit 202 and the A/D conversion unit 116. The signal processing control unit 702 instructs the analog signal processing unit 703 to remove frequency components of a constant frequency or higher from the analog electric signal 122 to satisfy the sampling principle by using an analog signal processing control signal 701. FIG. 11 shows an embodiment of the analog signal processing unit 703. The analog signal processing unit 703 is provided with one or more of frequency filtering circuits 802 having different frequency characteristics. The frequency filtering circuit 802 is an analog filtering circuit of a band-pass type. By instruction from the signal processing control unit 702, a switch control unit 803 arbitrarily changes connection states of the frequency filtering circuits 802 by a switching circuit 804 to thereby enable to select filters necessary for the processing.

Further, in order to realize similar function, in pace of the system of selecting necessary filtering circuits from a plurality of filtering circuits as in the embodiment shown in FIG. 11, there may be adopted a system in which by instruction of the analog signal processing control signal 701, the filter characteristic is changed by changing parameters determining the characteristic of the filtering circuit (when the filtering circuit comprises capacitor, resistor and inductor, capacitance, resistance, inductance and so on).

Figure 12:
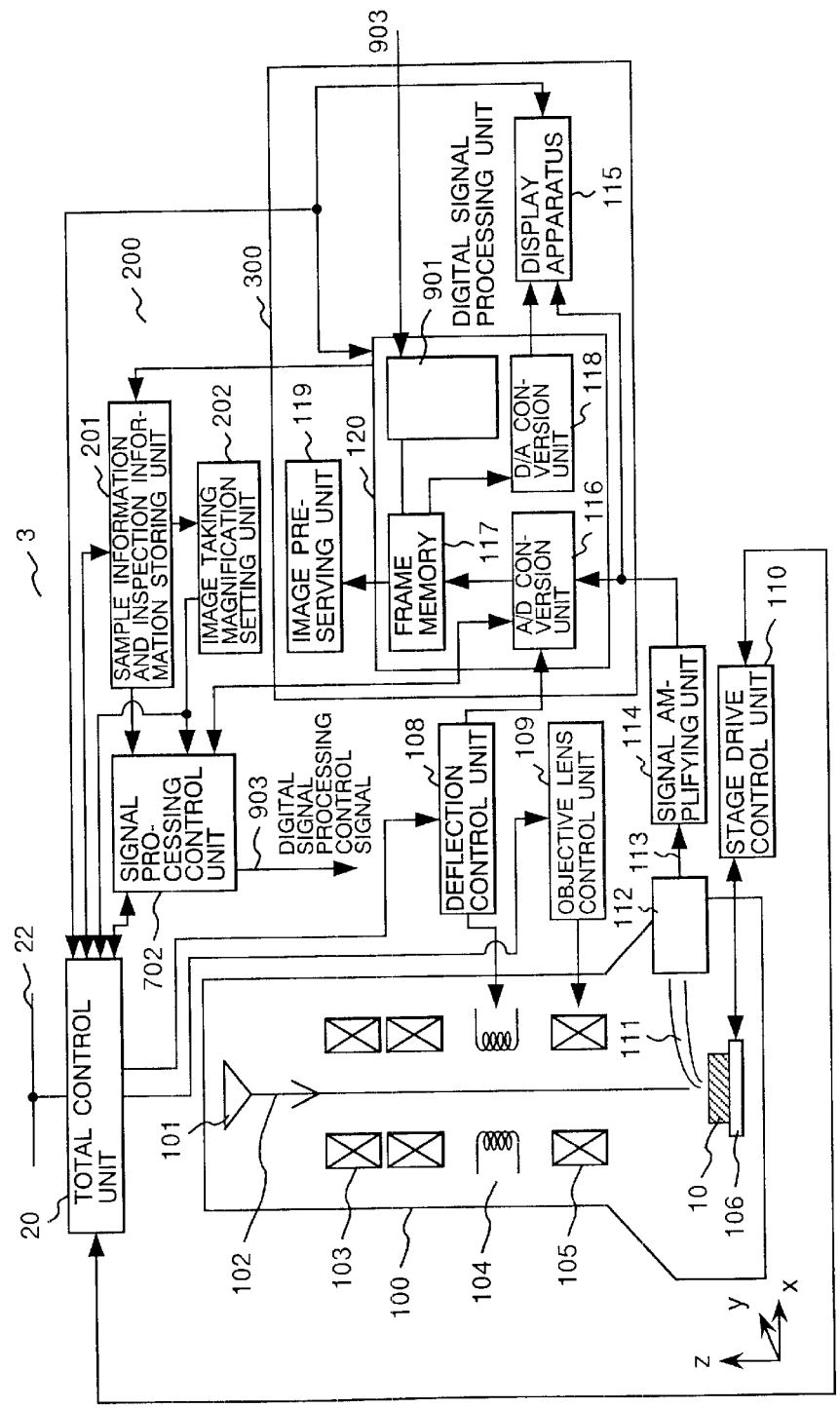
FIG. 12 is a schematic constitutional showing a fifth embodiment of a scanning electron microscope according to the present invention.
Figure 13:
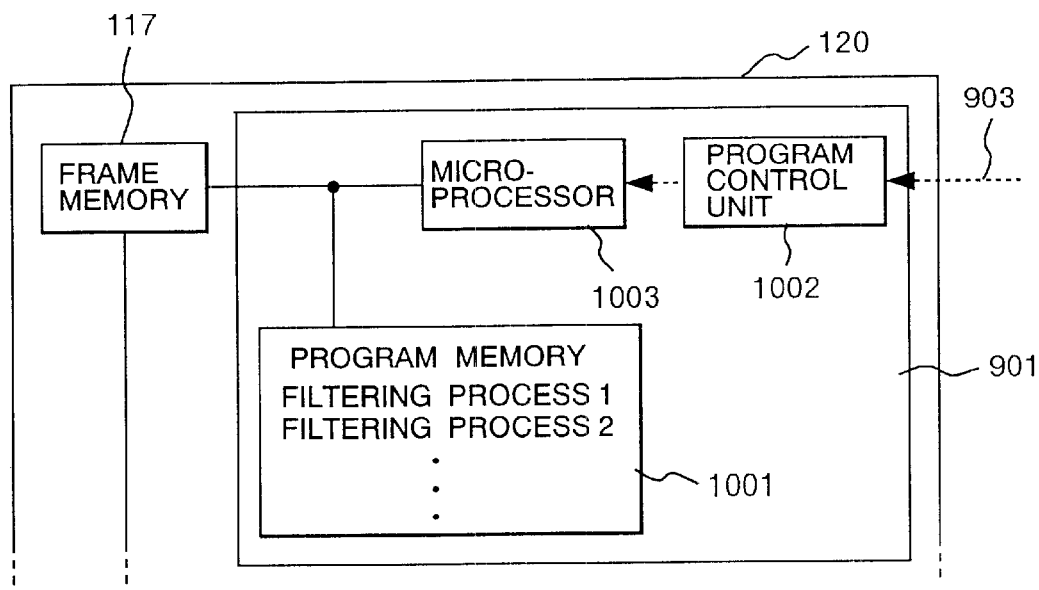
FIG. 13 is a diagram showing an embodiment of a specific constitution of a digital signal processing unit shown in FIG. 12.

Next, description will be given of a fifth embodiment of a scanning electron microscope for automatically sampling defect image according to the present invention with reference to FIG. 12. In order to carry out digital processing such that pseudo data (pseudo noise) is not caused in electron beam image taken with low magnification, it is an object of the fifth embodiment to specify the position of defect portion within the field of view of low magnification by carrying out a digital frequency filtering processing in respect of A/D-converted digital data at the A/D conversion unit 116 in conformity with image taking conditions to thereby provide a digital image signal of low magnification indicating true defect portion. A digital signal processing unit 901 for carrying out digital signal processing is provided in the image processing unit 120. FIG. 13 shows an embodiment of the digital signal processing unit 901. The digital signal processing unit 901 includes a microprocessor 1003 capable of making access to the frame memory 117, a program memory 1001 stored with programs of processings carried out by the microprocessor and a program control unit 1002 for controlling the microprocessor 1003 to carry out the processings based on instruction provided from digital signal processing control signal 903. The program memory 1001 is previously stored with one or more of digital filtering programs having different frequency characteristics. According to the embodiment shown in FIG. 12 and FIG. 13, the signal processing control unit 702 instructs the signal processing unit 120 having such a digital signal processing unit to determine a program for processing image data on the frame memory 117 by using the digital signal processing control signal 903 based on information concerning the sampling interval and so on from the sample information and inspection information storing unit 201, the image taking magnification setting unit 202 and the A/D conversion unit 116. The program control unit 1002 receives instruction of the digital signal processing control signal 903 and :selects and starts a program stored in the program memory 1001 for processing the microprocessor 1003 as instructed. Thereby, there can be carried out processings having filter characteristics which differ in accordance with various image taking conditions. Further, the constitution of the above-described embodiment is effective even when programs stored to the program memory 1001 are not filter programs.

As described above, upon taking image with low magnification, the control is facilitated by acquiring digital image indicating the defect portion by controlling to prevent pseudo noise components from being produced by irradiating the surface of the sample with the electron beam 102 in the defocused state as in the first, the second and the third embodiments rather than acquiring digital image indicating defect portion by removing pseudo noise components by filtering processing from a detected analog image signal or A/D-converted digital image signal as in the fourth and the fifth embodiments. Various kinds of patterns formed on the object substrate are conceivable and various kinds of filtering processings needs to provide in compliance with the kinds of patterns and image indicating defect portion needs to be prevented from being erased. Therefore, according to the fourth and the fifth embodiments, the filtering processing becomes complicated.

Next, description will be given of control information (sample information and inspection information inputted to the total control unit 20 and stored to the sample information and inspection information storing unit 201 as well as image taking magnification set to the image taking magnification setting unit 202 and so on) for taking electron beam image under conditions satisfying the sampling principle in respect of various products of semiconductor wafers in the scanning electron microscope having the function of automatically sampling defect image according to the present invention with reference to FIGS. 14(*a*) and 14(*b*).

FIGS. 14(*a*) and 14(*b*) show control information comprising sample information and inspection information inputted to the total control unit 20 and stored to the sample information and information storing unit 201 as well as image taking magnification set to the image taking magnification setting unit 202 and so on. Columns of product names indicated in FIG. 14(*a*) show an example with objects of five product kinds (kinds of samples) of Memory A (cell pitch is about 5 $\mu$m, frequencies of a background pattern formed on the surface are high), Memory B (cell pitch is about 15 $\mu$m and frequencies of a background pattern formed on the surface are low), Logic C, Logic D, Logic E mixed with memories (cell pitch is about 15 m, frequencies of a background formed on the surface are low). A column of "Presence or absence of memory cell" is a field showing whether or not respective products are provided with patterns of memory cells (frequency information on a background pattern at the defect portion concerning sample). "Cell pitch" indicates a cell pitch (design information concerning sample) when the product is provided with a memory cell. "Image taking magnification" is set with respective magnifications in low magnification and high magnification. In this case, the low magnification is determined to about 10,000 or lower such that the field of view becomes about several through 10 $\mu$m in accordance with the error between the coordinate system inspected and detected by the appearance inspecting apparatus and the coordinate system in the electron microscope. To be more specific, the appearance inspecting apparatus is provided with various pattern inspecting apparatus and foreign particle inspecting apparatus including a difference in fabrication maker and accordingly, as inspection information, there are name of kind of the appearance inspecting apparatus and the position coordinate of the defect portion. To be more specific, the low magnification signifies image taking magnification having low magnification (about 10,000 or lower such that the field of view becomes about several through 10 $\mu$m) which is used for specifying defect portion by difference image processing and the high magnification signifies magnification (equal to or higher than 10,000, for example, about 30,000 through 60,000) in taking image providing high resolution by high magnification to carry out further detailed analysis of the specified defect portion. The magnification in taking image with low magnification is determined by inputting it by the user to the total control unit 20 as the magnification capable of disposing defect of image taking object within the field of view of image having low magnification in consideration of the error of internal coordinate between various kinds of appearance inspecting apparatus and the scanning electron microscope.

The magnification in taking image with high magnification is a value determined by inputting it by the user to the total control unit 20 in consideration of resolution of image necessary for detailed analysis of defect. Columns of "Control conditions" are control conditions determined to control to take image in a state of satisfying the sampling principle from four values of "Product name", "Presence or absence of memory cell", "Cell pitch" and "Image taking magnification".

FIG. 14(*b*) shows a table showing how to control specifically for respective control conditions. According to the example, Condition 1 signifies to set z direction position of the stage to 0 (mm) and beam current to 1.0 (pA) under a condition of irradiating electron beam to the surface of the object substrate 10 in a focused state as shown in FIG. 6(*a*) in order to adapt to image taking at high magnification. Condition 2 shows an example of a case of setting z direction position of the stage to 10 (mm) and beam current to 1.5 (pA) under a condition in which electron beam is irradiated to the surface of the object subject 10 by reducing an amount of defocusing as shown in FIG. 6(b) to adapt to Memory B or Logic E mixed with memory in taking image with low magnification. Condition 3 shows an example in a case of setting z direction position of the stage to 20 (mm), and beam current to 2.0 (pA) under a condition in which electron beam is irradiated to the surface of the object substrate 10 by increasing the amount of defocusing as shown in FIG. 6(b) to adapt to Memory A. Further, control conditions 2 and 3 show conditions in which electron beam is irradiated to the surface of the sample in the defocused state by increasing both of the z direction position of the stage and the beam current, however, it is apparent that either of them may be increased. To be more specific, a number of these tables are stored and prepared to a memory apparatus (not illustrated) of the total control unit 20 or the beam spot diameter control unit 203 or the signal processing control unit 702 and the total control unit 20 or the beam spot diameter control unit 203 or the signal processing control unit 702 can uniquely determine control conditions in taking image of different products with different magnifications by referring to these tables.

According to the tables shown in FIGS. 14(a) and 14(b), both of Logic C and Logic D are not provided with memory cells in the pattern and accordingly, control conditions of image taking magnifications at low magnification and at high magnification are equal to "Condition 1". This signifies that since the circuit patterns are not provided with memory cell portions, even when the electron beam diameter is not controlled by the difference in the magnification, there causes no noise, and electron beam image is taken by the detector 112 and can be A/D-converted by the A/D conversion unit 116. Further, both of Memory A and Memory B are provided with memory cells as their patterns; however, there is observed a difference in cell pitches thereof. Therefore, according to Control condition 1 in taking image of Memory A having a smaller cell pitch with low magnification, compared with Control condition 2 in taking image of Memory B with low magnification, an amount of moving the stage 106 and a value of beam current become large, that is, indicating that image is to be taken under a further defocused state. Further, Logic E mixed with memories is provided with a cell pitch of a pitch of about 15 $\mu$m in its circuit pattern and therefore, the control condition is equal to the control condition of Memory B.

Further, the image taking conditions of all the products in taking image with high magnification are equal to "Control condition 1" because the image taking condition of "Control condition 1" signifies a condition in the case in which the electron beam diameter on the sample is minimum, that is, electron beam image is taken with high resolution without dimming the electron beam image.

The tables shown in FIGS. 14(a) and 14(b) are generalized into content shown in FIGS. 15(a) and 15(b). To be more specific, conditions of taking electron beam image are constituted by kinds of object substrates (sample) where defect portions are present and the position information stored to the sample information and inspection information storing unit 201, image taking magnifications (basically, comprising low magnifications and high magnifications) set to the image taking magnification setting unit 202, sampling intervals for converting analog image signals into digital image signals at the A/D conversion unit 116 and so on. On the other hand, as control patterns for taking electron beam image, there are a distance of moving the stage, a numerical aperture of the objective lens and beam current for changing a focused condition for irradiating electron beam to the surface of the sample and analog filters and digital filters for filtering processing.

In this way, when a corresponding relationship between image taking conditions shown in FIG. 15(a) and control patterns shown in FIG. 15(b) is previously stored to the total control unit 20 or the beam spot diameter control unit 203 or the signal processing control unit 702 and prepared as tables, the total control unit 20 or the beam spot diameter control unit 203 or the signal processing control unit 702 can select control patterns in accordance with image taking conditions adapted to defect portions of object:substrates (samples) charged into the electron microscope.

FIG. 2 shows a mode in which the scanning electron microscope 3 according to the present invention and one or more of appearance inspecting apparatus 2 are connected to the network 22. The scanning electron microscope 3 is provided with an inspection information receiving unit 1202 so that inspection information provided from various kinds of the outlook inspect ion apparatus 2 can be received via the network. The inspection information may be supplied via other computer such as the fabrication line control apparatus 1205 connected to the network 22 and controlling a fabrication line or may be transferred directly from the appearance inspecting apparatus 2. The inspection information includes all of information provided by the appearance inspecting apparatus 2 and signifies, for example, positions of detected defects in the object substrate or defect sizes. The inspection information is inputted and stored to the sample information and inspection information storing unit 201 via the total control unit 20 in the scanning electron microscope 3. The sample information and inspection information storing unit 201 can also store information on design values of circuit patterns formed on the object substrate and so on other than the inspection information. Considering detailed observation of defects detected by various kinds of the outlook inspection apparatus 2 by using the scanning electron microscope 3, there are normally a plurality of defects to be observed in one object substrate and accordingly, enormous laborious effort is required to take all of the images. According to the present invention, it is possible to calculate a maximum spatial frequency of a pattern at a surrounding of each defect portion from the position of each defect and a design value of a circuit pattern formed on the object substrate, to set magnification in image taking, to control electron beam in a defocused state in order to prevent pseudo noise from being produced and to thereby take digital electron image by filtering processing. When the apparatus is operated to continuously take images of other defects after taking image of one defect, even in the case in which a number of defect portions are present in one object substrate, with no manual operation, positions of defect portions for all of the defect portions can be specified and digital electron beam image having high resolution of the specified defect portions can be acquired to thereby carry out detailed analysis. Other than the mode shown in FIG. 2, similar effect is achieved even when the network 22 is connected not only with the appearance inspecting apparatus 2 but also with other inspecting apparatus (for example, a tester for carrying out operating test of each chip formed on the object substrate) and one or more of observation apparatus constituted by the microscope according to the present invention and so on.

Next, FIG. 16 is a diagram for explaining a role of a defect automatic sampling apparatus according to the present invention playing in a semiconductor fabrication process.

According to a semiconductor fabrication process, semiconductors are fabricated after having been subjected to several hundreds of processes 1 through n (P1 through Pn) and there is a case in which a time period of about 100 days is required to finish them. However, the acceptability of product is determined in Probe inspection 1 after finishing with all the processes. Accordingly, in order to promote the yield, means for predicting the acceptability of intermediate processes is indispensable. Therefore, outlook inspection of the object substrate to be inspected (wafer substrate) is carried out by the defect inspecting apparatus 2 comprising an optical pattern defect inspecting apparatus and a foreign particle defect inspecting apparatus and the acceptability of process is determined by abnormality of outlook such as defect of wiring patterns or foreign particle defects. When the abnormality of process is confirmed, a countermeasure needs to be carried out and a defect automatic image classifying apparatus 3 plays an important role as information sampling means therefor.

To be more specific, since progress in miniaturization of wiring patterns in semiconductor wafers or the like is remarkable, a defect size to be detected tends to be further downsized to 0.2 $\mu$m or smaller and accordingly, there is. brought about a situation in which although locations and numbers of defects can be grasped from a result 4 of outlook inspection inspected by the optical defect inspecting apparatus 2, information on properties of defects or the like cannot be provided. Hence, based on locations (position coordinates) of defects on the object substrate to be inspected provided as the result 4 of the outlook inspection, properties (categories) of defects are classified and outputted by referring to instruction data based on characteristic amounts (size, shape, surface texture, gray scale value and so on of defect portion) of an image 5 of a portion where defect is caused by the defect automatic image classifying apparatus 3. Then, in a quality control system 7, countermeasure candidates can be narrowed down by confirming whether or not the defects are defects serious to the process based on properties (categories) of the defects classified by the defect automatic image classifying apparatus 3. An example shown by numeral 6 of FIG. 16 shows a result of summarizing again a result of classifying defect images according to kinds (categories) of defects. According to the classification 6, defect kinds are schematically indicated by two kinds of pattern defect and foreign particle defect. According to the result 6 provided from the defect image classifying apparatus 3, in the quality control system 7, it is known to be preferable to carry out a countermeasure for preventing foreign particles from being produced since an occurrence frequency of foreign particles is larger than that of pattern defects. To be more specific, in the quality control system 7, promotion of the yield can swiftly be achieved by predominantly predicting cause of defect having a high occurrence frequency and establishing a countermeasure against the defect.

The automatic image sampling apparatus 3 according to the present invention realizes automatic sampling of defect images for review, that is, an image sampling function capable of stably catching defects with the purpose of promoting efficiency of defect confirming operation or reviewing operation which has been carried out optically.

Next, description will be given of a constitution of the automatic image sampling apparatus 3 constituted by the scanning electron microscope according to the present invention. The total control unit (host computer) 20 controls a transfer apparatus 8 via a transfer control unit 17 to thereby mount the object substrate (for example, wafer substrate) 10 on the stage 106 capable of moving (traveling) in X-Y axes directions. In the meantime, there is acquired information for specifying the object substrate 10 inputted from a wafer ID reading apparatus installed at the transfer apparatus 8 or inputted by a user via a keyboard or the like and the host computer 20 receives defect coordinate information in correspondence thereto from a higher system via the network 22. The defect coordinates information is related to all of points of defect coordinates outputted from the defect inspecting apparatus (appearance inspecting apparatus) 2 shown in FIG. 1 or points of defect coordinates narrowed down for defect review or for sampling defect images from a result outputted from the defect inspecting apparatus 2. The higher system indicates a quality control system of a yield control system, a fabrication line monitoring system, a process control system and so on or an inspection apparatus for inspecting defects. The host computer 20 transmits instruction to the stage control unit 16 by referring to the defect coordinates information to move the stage 106 so that defects are moved to observing positions. Images of defects are taken by the electron detector 112 and defect images are recorded in an image recording apparatus (image storing apparatus) 14 via an image inputting apparatus 13. The above-described processings are repeated with respect to designated defects and defect images taken for defect portions present on the object substrate 10 are accumulated in the image recording apparatus 14. Further, the total control unit (host computer) 20 is also inputted with kind names and classification names of defect inspecting apparatus inspecting object substrates charged into the automatic image sampling apparatus 3 directly from the appearance inspecting apparatus 2 or from a control system controlling a total of the fabrication line via inputting means 21 of a record medium or the like or the network 22 and the information is stored to a storing apparatus 23. Therefore, the total control unit (host computer) 20 can grasp also information on so that defect inspecting apparatus the charged object substrates have been inspected.

In the case of a scanning electron microscope 90, electron beam image can be acquired as highly fine outlook image having high resolution. The scanning electron microscope 90 is constituted by the detecting unit 100 and the image inputting unit 13. An electron optical system in the detecting unit 100 is constituted by the electron gun 101, an electron beam pulling electrode (not illustrated), the condenser lens (converging lens) 103, a blanking deflector (not illustrated), a diaphragm (not illustrated), the scanning deflector 104, the objective lens 105, a reflecting plate (not illustrated) for reflecting detected electron, an ExB deflector (not illustrated) and a Faraday cup (not illustrated) for detecting the beam current. The reflecting plate is formed in a conical shape and provided with the secondary electron multiplying effect. In the electron detecting unit, the electron detector 112 for detecting electron of, for example, secondary electron, reflected electron, absorbed electron or the like is installed, for example, above or below the objective lens 105. Further, an output signal from the electron detector 112 is amplified by the amplifier 114.

Inside a sample chamber are installed a sample base 97 for mounting the object substrate (substrate for instruction) 10 for acquiring highly fine outlook image having high resolution, the stage 106 for moving the sample base 97 in X-Y axes directions, a length measuring instrument for monitoring position (not illustrated) for measuring a position of the stage and a height measuring instrument for measuring height (not illustrated) for measuring a height of the object substrate 10. The position monitoring length measuring instrument measures the position of the stage 106 or the like and transfers the result to the total control unit 20. Therefore, the total control unit 20 can accurately grasp an area and a position to which the electron beam 102 is irradiated based on these data. Further, the storing apparatus 23 is stored with information on outline position coordinates (outline position data (xn, yn)) of defect, number of defects and dimensions of each defect in respect of the object substrate (including substrate for instruction) in which various defects of defects of foreign particles or wiring patterns (circuit pattern) inspected by the optical defect inspecting apparatus (foreign particle inspecting apparatus or pattern inspecting apparatus) 2 are present. Therefore, when the object substrate 10 in which various defects such as foreign particles or wiring patterns inspected by the optical defect inspecting apparatus 2 are present is mounted on the stage 106, the total control unit 20 can position defects within a wide area (wide field of view) to which the electron beam 102 is irradiated by controlling the stage 106 based on the outline position data of defect stored to a storing apparatus 23 and the position coordinates of the stage 106 or the like measured by the position monitoring length measuring instrument stored to the storing apparatus 23.

The height measuring instrument measures the height of the object substrate 10 mounted on the stage 106 by using optical measuring instruments and the like. Further, based on the height data measured by the height measuring instrument, the focal length of the objective lens 105 for finely narrowing the electron beam is dynamically corrected and the electron beam can be irradiated always in a state in which the observation area is focused.

The electron beam emitted from the electron gun 101 is narrowed to a beam diameter of about a pixel size on a sample face via the condenser lens 103 and the objective lens 105. At this occasion, negative potential is applied to the object substrate 10 by a ground electrode 95 and a retarding electrode 96 and the electron beam is decelerated between the objective lens 105 and the object substrate 10 so that high resolution formation in a low acceleration voltage area is achieved. When the electron beam 102 is irradiated, electrons are generated from the object substrate 10. By detecting electrons generated from the object substrate in synchronism with repeated scanning of the electron beam 102 by the scanning deflector 104 in X direction and continuous movement of the object substrate 10 by the stage 106 in Y direction, highly fine two-dimensional electron beam image of the object substrate is provided. Electrons generated from the object substrate are caught by the electron detector 112 and signals therefrom are amplified by the amplifier 114. In this case, as the scanning deflector 104, an electrostatic deflector having fast deflecting speed may preferably be used. Further, as the electron gun 101, a thermofield emitting type electron gun capable of increasing the electron beam current and capable of shortening an irradiation time period may preferably be used. Further, as the electron deflector 112, a semiconductor detector capable of driving at high speed may preferably be used.

The image inputting unit 13 is constituted mainly by an A/D converter 131 and a preprocessing circuit 132. Further, an electron detecting signal detected by the electron detector 112 is amplified by the amplifier 114 and converted into digital image data (gray scale image data) by the A/D converter 131. The converted digital image data is transferred by, for example, transferring means (optical fiber cable) and inputted to the preprocessing circuit 132. At the preprocessing circuit 132, there are carried out correction of dark level, correction of fluctuation of electron beam and correction of shading and picture quality is improved by carrying out a filtering processing for erasing pseudo noise components.

As is described above, according to the scanning electron microscope 90, by mounting on the stage 106 the object substrates (substrates for instruction) 10 which are provided from various fabrication processes and in which various fine defects having different dimension (size) and states are present, the fine defects are positioned within a wide area (wide field of view) to which the electron beam 102 is irradiated and very fine outlook images by electron images of the defects are acquired by the electron detector 112 and the amplifier 114 and inputted to the image inputting unit 13 and accumulated in the image storing apparatus 14.

As is described above, when a relationship between a stage coordinate system of the defect inspecting apparatus 2 and the object substrate coordinate system is the same as that between the stage coordinate system of the automatic image sampling apparatus 3 and the object substrate coordinate system, by determining position on the object substrate by using the same alignment marks on the object substrate (wafer substrate) 10, there poses no problem in acquiring image of defect by the automatic image sampling apparatus 3 by using defect coordinate values of defects to be observed outputted. from the defect inspecting apparatus 2. However, in reality, it is difficult to share defect coordinates between the defect inspecting apparatus 2 and the automatic image sampling apparatus 3. As reason therefor, there are pointed out a difference in a relationship between stage coordinate systems in respective apparatus and a coordinate system on the object substrate, an error in braking stages in the respective apparatus and so on. Further, there also poses a problem in which marks for carrying out alignment are not present in an object substrate which is not formed with a pattern such as a face plate or the like.

There is disclosed a method of carrying out alignment by using defects present on an object for observation when there are no common alignment marks or when there is present a deviation on coordinates between the defect inspecting apparatus 2 and the automatic image sampling apparatus 3 in Japanese Patent Laid-open No. 6-249790.

In the meantime, in order to take image of defect by moving the stage 106 to a position of a designated defect under a state in which alignment is not carried out accurately, the image taking magnification must be lowered, and an image must be taken in a wide range to thereby catch the defect in the image. However, it is difficult to detect a fine defect by low magnification. Hence, when a defect is utilized to carry out alignment, by predominantly using a defect having a large defect size, the defect can firmly be detected even by the low magnification. Hence, the total control unit (host computer) 20 rearranges information on defect coordinates acquired from the defect inspecting apparatus 2 inputted via, for example, the network 22, or inputted by the inputting means 21 of a record medium or the like and stored to the storing apparatus 23 in an order of large to small in accordance with dimensions of respective defects, takes images of defects by the image detector 12 or the electron detector 112 and inputs signals to the image inputting unit 13, converts them into digital image signals at the image inputting unit 13, further carries out correction of dark level, correction of fluctuation of electron beam and correction of shading in respect thereof and stores them to the image storing apparatus 14 after carrying out a filtering processing for erasing pseudo noise components so that the defects can be detected even when images thereof are initially taken with low magnification. Therefore, the defects can be used for the purpose of alignment and after finishing the alignment, the positioning accuracy of the defects by the stage 106 is promoted and accordingly, the defect images can be acquired with higher magnification. To be more specific, defect images can be acquired with pertinent magnification also with respect to very fine defects.

Next, description will be given of a first embodiment of an operation flow in which the automatic image sampling apparatus 3 acquires defect images with higher magnification based on position coordinates of defects, a number of defects on an object substrate and dimensions of defects provided form the defect inspecting apparatus 2 with reference to FIG. 18.

First, in step S401, a memory unit 24 of ROM or the like is inputted with a number N of defects on an object substrate used for alignment by converting coordinates of positions of the defects provided from the defect inspecting apparatus 2 into a coordinate system of the automatic image sampling apparatus 3 and image taking magnification for sampling the defect with dimensions of the defects provided from the defect inspecting apparatus 2 as a reference (defect sampling magnification for defect dimension) previously by using the inputting means 21 and the number and the image taking magnification are stored and set to the memory unit 24 of ROM or the like. To be more specific, previously, the number N of defects on the object substrate used for alignment (N is equal to about 5 through 10 to be able to carry out alignment in the coordinate system of the automatic image sampling apparatus 3) and the image taking magnification for extracting defects with defect dimensions provided from the defect inspecting apparatus 2 as a reference (defect sampling magnification for defect dimension), may be set to the memory unit 24 of ROM or the like and prepared as tables. Further, as data with. respect to defect sampling magnification for defect dimension which is. set to the memory unit 24 of ROM or the like, there are conceivable a method of classifying defect dimensions provided from the defect inspecting apparatus 2 in accordance with sizes thereof and defining image taking magnification for respective classes and a method of setting image taking magnification such that sizes of defects relative to image fall in a constant size or a constant size range.

According to the former method, defects are classified such that Class α includes defects, for example, less than 0.5 m, Class β includes defects, for example, equal to or more than 0.5 $\mu$m and less than 1 $\mu$m, Class γ includes defects, for example, equal to or more than 1 $\mu$m and less than 5 $\mu$m and Class δ includes defects equal to or higher than 5 $\mu$m and image taking magnifications are allocated to the respective classes such that the Class α is allocated with 50,000 (for example, image of defect of 0.1 $\mu$m is taken as a digital image signal of 5 mm), the Class β is allocated with 30,000 (for example, image of defect of 0.5 $\mu$m is taken as a digital image signal of 15 mm), the Class γ is allocated with 10,000 (for example, image of defect of 1 $\mu$m is taken as a digital image signal of 10 mm) and the Class δ is allocated with 30,000 (for example, image of defect of 5 $\mu$m is taken as a digital image signal of 15 mm). Further, it is possible to set these such that the image taking magnification is not allocated to a specific class and image of a defect in correspondence with the class is not taken. For example, in the above-described example, the Class δ includes defects, for example, equal to or more than 5 $\mu$m and less than 10 m, and further, Class E is provided to defects of, for example, 10 $\mu$M or more. And, image of defects in correspondence with Class E (in the case of 3,000, for example, image of defect of 10 $\mu$m is taken as a digital image signal of 30 mm) is not taken. Thereby, image taking can be prohibited with respect to a defect having very large dimensions and protruding from the field of view of image. Further, as mentioned above, there is a scanning electron microscope for providing image taking magnification of about 3,000 through 50,000.

According to the latter method, a size of a defect observed on an image is previously designated by an image size (unit: pixel). For example, when pixel resolution is set to Y $\mu$m in an image having magnification of X and a defect size in image (unit: pixel) is designated as Z pixels, image taking magnification D for taking image of a defect having a dimension of C $\mu$m is given by D=(CX)/(YZ). The same goes by designating it by a rate to image. Further, when a constant width is permitted in a designated value of a defect size on image, a constant width is permitted also to image taking magnification and therefore, image taking magnification may be selected within a permitted range.

Next, in step S402, position coordinates of defects and dimension information on defects in respect of the defects having the defect number M on the object substrate 10 which are inputted from the defect inspecting apparatus 2 to the automatic image sampling apparatus 3, are read by using the network 22 or the inputting means 21 of a record medium or the like and stored and accumulated to the storing apparatus 23.

Next, in step S403, the total control unit (host computer) 20 rearranges the defects in an order of large to small of defect dimension based on the dimension information on the defects having the defect number M on the object substrate 10 which are stored and accumulated to the storing apparatus 23 and inputted to the automatic image sampling apparatus 3 and registers the rearranged order to the storing apparatus 23 as an image sampling order n at the automatic image sampling apparatus 3. Further, the defect number on the object substrate 10 inputted to the automatic image sampling apparatus 3 is M and accordingly, the defect number as object of image taking at the automatic image sampling apparatus 3 becomes M.

Further, the object substrate 10 is loaded onto the stage 106 by the transfer apparatus 8.

Next, in step S404, the total control unit (host computer) 20 designates n=1 for the image sampling order n as an order having a large defect dimension on the object substrate 10 which is recorded and accumulated to the storing apparatus 23 and inputted to the automatic image sampling apparatus 3.

Next, in step S405, the total control unit (host computer) 20 controls to drive a stage control unit 16 based on position coordinates of defects from the order n=1 having a large defect dimension stored to the storing apparatus 23 so that the stage 106 mounted with the object substrate 10 is moved and the defect n is positioned on the optical axis such that image of the defect n disposed at coordinates (Xn, Yn) on the object substrate can be taken by the electron detector 112.

Next, in step S406, the total control unit (host computer) 20 selects the defect sampling magnification in correspondence with the defect dimension starting from the order n=1 having a large defect dimension stored to the storing apparatus 23 from tables set to the memory unit 24, performs the control to provide low magnification by switching the detecting system to the detecting system (112 etc.) having low magnification or enlarging a scanning deflection amount by the scanning deflector 13 (may be combined with scanning of the stage 106) to thereby provide the selected magnification and takes image of the defect by low magnification. The position coordinates (Xn, Yn) of the defect can be detected by the coordinate system of the automatic image sampling apparatus 3 by enabling to position the defect having such a large dimension within the field of view of image taking with low magnification. Further, in the case of the scanning electron microscope 90, a sampling period for carrying out digital conversion at the A/D converter 131 is made constant both in taking image with low magnification and taking image with high magnification. When the sampling period is made constant in this way, in the case of low magnification, the sampling interval is widened and: the resolution becomes lower than that in high magnification. However, the image taking magnification is determined in compliance with the defect dimension and accordingly, the same resolution can be provided to the defect dimension. However, the sampling period can be changed in accordance with the image taking magnification.

To be more specific, in step S406, the total control unit (host computer) 20 controls the scanning deflection amount of the scanning deflector 13 (may be combined with scanning of the stage 106) such that images of defects having defect dimensions from an initial largest one to N-th (N=5 through 10) set to the memory unit 24 are taken by image taking magnification in correspondence with the defect sizes so that the images of the defects from the initial largest one to N-th are taken by the electron detector 112 by the defect sampling magnification in correspondence with the defect dimensions, inputted to the image inputting unit 13, converted to digital image signals at the image input unit 13, subjected to correction of dark level, correction of fluctuation of electron beam and correction of shading and stored to the image storing apparatus 14 after carrying out filtering processing for erasing pseudo noise components. In this way, the images of the defects from the largest one to N-th are taken in accordance with the coordinate system of the automatic image sampling apparatus 3 and accordingly, the alignment in accordance with the coordinate system of the automatic image sampling apparatus 3 is also carried out. The image taking magnification at this occasion may use fixed magnification or variable magnification (provided by controlling the scanning deflector 104) which is low magnification set and stored to the memory unit 24 for taking defect image for alignment.

Next, in step S407, based on instruction from the total control unit (host computer) 20, for example, with image at the same location of a contiguous chip taken as reference image, images of defects having defect dimensions of an initial largest one to N-th which are set to the memory unit 24, are taken with defect sampling magnification in correspondence with the defect dimensions, inputted to the image inputting apparatus 13 and stored to the image recording apparatus (image storing apparatus) 14. As a result, an image processing apparatus 15 (120) samples difference images produced by defect images showing defects having defect dimensions from a largest one to N-th stored to the image recording apparatus 14 (119) and reference images, converts the difference images showing the sampled defects into, for example, binarized image signals and calculates, for example, positions of centers of gravity or central positions in X direction and Y direction from the converted binarized image signals showing defects to thereby detect positions of the defects and transmitted to the total control unit (host computer) 20. The total control unit (host computer) 20 can provide defect position coordinates (Xn, Yn) on the object substrate by converting the coordinate system into a reference coordinate system of the stage 106 measured by the position monitoring length measuring instrument (which is also a reference coordinate system on the object substrate 10 since the object substrate 10 is positioned and mounted onto the stage 106) based on position data of the defects in the images detected by the image processing apparatus 15. Further, in this case, it is possible that the total control unit (host computer) 20 controls to take a representative alignment mark formed on the object substrate 10 similar to the above-described and a central position of the alignment mark is calculated by the image processing apparatus 15 so that the defect position coordinates (Xn, Yn) are provided with the alignment mark as a reference and stored to the storing apparatus 23.

At step S409, the total control unit (host computer) 20 outputs instruction to repeat the above-explained processings until n reaches N (about 5 through 10) set to the memory unit 24 to thereby provide N sets of pairs of coordinates [(xn, yn), (Xn, Yn)]. (xn, yn) designates a position of a defect detected by the coordinate system of the defect inspecting apparatus (appearance inspecting apparatus) 2, and (Xn, Yn) designates a position of the defect detected by the coordinate system of the automatic image sampling apparatus 3 and a difference between the two coordinates is accordingly a deviation of coordinate systems between the defect inspecting apparatus 2 and the automatic image sampling apparatus 3. Hence, the total control unit (host computer) 20 derives a correlation equation between the two coordinate systems by using N sets of coordinate pairs to thereby enable to convert position coordinates of the defect inspecting apparatus 2 into position coordinates of the automatic image sampling apparatus 3. There are. present rotational and offset deviation between the two coordinate systems and therefore, an equation of converting (xn, yn)→(Xn, Yn) is represented by Equation (3) shown below.

$$\begin{bmatrix} Xn \\ Yn \end{bmatrix} = \begin{bmatrix} A & -B \\ B & A \end{bmatrix} \begin{bmatrix} xn \\ yn \end{bmatrix} + \begin{bmatrix} C \\ D \end{bmatrix} \qquad (3)$$

Hence, the total control unit (host computer) 20 can calculate A, B, C and D from N sets of coordinate pairs [(xn, yn), (Xn, Yn)]. In calculating these, offsets (C, D) is calculated from respective positions of centers of gravity of (xn, yn) and (Xn, Yn) and thereafter, A and B may be calculated by least square method utilizing a quasi-inverse matrix. In this way, the total control unit (host computer) 20 can calculate deviation correcting coefficients (A, B, C, D) in respect of the position coordinates (xn, yn) of the defect inspecting apparatus 2 for calculating the position coordinates (Xn, Yn) of the automatic image sampling apparatus 3.

Next, in step S410, the total control unit (host computer) 20 calculates the defect position coordinates (Xn, Yn) on the object substrate 10 in the coordinate system of the automatic image sampling apparatus 3 by carrying out deviation correction by using the conversion equation shown by Equation (3), as mentioned above, in respect of the defect position coordinates (xn, yn) stored to the storing apparatus 23 and provided to the defect inspecting apparatus 2 with regard to defects which become smaller successively after n=N+1 to M-th.

Next, in step S411, the total control unit (host computer) 20 controls the stage control unit 16 to move the stage 106 such that the defect n is positioned (aligned) to the optical axis so that an image thereof can be taken by the electron detector 112 in accordance with an order of sampling image with regard to the defect n which becomes smaller successively from n=N+1 to M-th. Next, in step S412, the total control unit (host computer) 20 selects image taking magnification in correspondence with a dimension of the defect n stored to the storing apparatus 23 from the correlation table between a defect dimension and image taking magnification stored to the:memory unit 24, controls the scanning deflection amount by the scanning deflector 13 (may be combined with scanning by the stage 106) such that the image can be taken by the selected image taking magnification, and takes the image by the electron detector 112 by the defect sampling magnification in correspondence with the dimension of the image of the defect n. A signal of the taken defect image is inputted to the image inputting unit 13, converted into a digital defect image signal at the image inputting unit 13 and stored to the image storing apparatus 14 after carrying out various correction or noise removal. To be more specific, by carrying out the deviation correction to the coordinate system of the automatic image sampling apparatus 3, the defect n which becomes. smaller successively from n=N+1 to M-th present on the object substrate 10 can be positioned (aligned) within the field of view of image taking magnification in correspondence with the dimension and the image of the defect n can be taken by the image taking magnification in correspondence with the dimension.

Next, in step S413, a successive defect (n=n+1) is designated in accordance with the order of sampling image, in step S414, when input of images of all the defects present on the object substrate is finished. Then, in step S415, the object substrate 10 is unloaded from the stage 106 by the transfer apparatus 8 and the operation proceeds to taking image of defect of a successive object substrate.

Although according to the above-described explanation, it is described that image is taken by the defect sampling magnification in correspondence with the defect dimension (defect size) based on the correlation table between the defect dimension stored to the memory unit 24 and the image taking magnification, for example, there may be used first fixed image taking magnification in taking images of defects for alignment of n=1 through N and second fixed image taking magnification for defects of n=N+1 through M. In this case, further detailed positional deviation correction can be carried out by using a defect image of which is taken by the first image taking magnification for alignment as mentioned above, positioning accuracy (alignment accuracy) of defects in taking image of defects of N+1-th and thereafter can be promoted. As a result, a dispersion of a positioned defect from the center of the field of view of image is reduced and image can be taken by the second image taking magnification with the field of view narrower than the field of view provided by the first image taking magnification, that is, higher magnification, that is, the second image taking magnification can be set to magnification higher than the first image taking magnification. In this way, by setting the second image taking magnification to magnification higher than the first image taking magnification, further fine defect can be caught with high resolution, characteristic amounts (size, shape, surface texture, gray scale value and so on) of further fine defect can accurately be extracted and can be classified by detailed analysis in respect of properties (categories) of the defect. Particularly, when the second image taking magnification is set to magnification at high as possible (for example, 50,000 (image can be taken as a digital image signal by a ratio of 0.02 μm to 1 mm) through 30,000 (image can be taken as a digital image signal with a ratio of 0.02 μm to 0.6 mm) or more) characteristic amounts of defect can accurately be sampled and properties (categories) of the defect can be classified by further detailed analysis.

Although an explanation has been given of a case in which the image taking magnification is switched in two stages in accordance with object of taking image of defect in the above-described specific examples, the classification may be carried out in accordance with defect dimension (defect size) as mentioned above, to thereby determine the image taking magnification in accordance with the class of the defect dimension. Further, there may be adopted a method of applying the image taking magnification for taking an image with the size of defect observed on image by using previously designated image size (unit: pixel).

Next, description will be given of a second embodiment of operation flow for acquiring image of defect with higher magnification based on position coordinates of defects, a number of detects on object substrate and dimensions of defects provided from the defect inspecting apparatus 2 with reference to FIGS. 19A and 19B.

Next, description will be given of points of difference between the second embodiment and the first embodiment shown in FIG. 18.

First, a first point resides in that in step S401', in addition to content of step S401, magnification of observing defect in correspondence with defect size calculated by the image processing apparatus 15 is inputted by using the inputting means 21 and stored to the memory unit 24 as a table. Magnification of sampling defect is determined to be as low as 10,000 or smaller such that large defect can be disposed within the field of view of taking image in consideration of the error between the coordinate system of the defect inspecting apparatus 2 and the coordinate system of the automatic image sampling apparatus 3. In respect of defect having a dimension smaller than that of the above-described defect, although the error is corrected between the coordinate system of the defect inspecting apparatus 2 and the coordinate system of the automatic image sampling apparatus 3, since position data (xn, yn) detected by the defect inspecting apparatus 2 also includes an error of detection, the magnification of sampling defect is obliged to determine to about 30,000 which is lower than 50,000 such that the defect having a small dimension can be disposed within the field of view of taking image. However, by detecting a position (Xn, Yn) by the coordinate system of the automatic image sampling apparatus 3 and repositioning (realigning) again the defect at the center (optical axis) of the field of view of taking image, magnification of observing defect for taking image of defect again is made higher than the magnification of sampling to thereby correspond to the defect size so that image of defect having higher resolution can be acquired.

A second point resides in that in step S407a, the image processing apparatus 15 calculates a difference image signal showing defect between a defect image signal provided in step S406 and a reference image signal, detects the position (Xn, Yn) of the defect from the calculated difference image signal and detects a size of the defect calculated by an area, lengths in X and Y directions and so on from a binarized image signal showing the defect.

A third point resides in that in step S407b, when the size of the defect detected by step S407a is larger than a size prescribed HUGE I, the defect is not made an object of sampling image and the order is skipped to a successive defect. This is because when the size of the defect is large and, for example, protruded from the field of view of taking image, accurate alignment cannot be expected.

A fourth point resides in that in step S407c, the position (Xn, Yn) of the defect detected in step S407a is repositioned to the center of the field of view, image of the defect is taken by. magnification of observing defect in accordance with the size of the defect which has been detected again, and a taken defect image signal is inputted to the image inputting unit 13 and stored to the image storing apparatus 14 after subjected to processings of various corrections and noise component erasure and so on to thereby acquire a digital image signal of large defect. Thereby, the digital image signal of large defect can be acquired with high resolution by taking image of defect with defect observing magnification of about 10,000 higher than the defect sampling magnification and accordingly, large defect can be classified by detailed analysis of characteristic amounts or properties of defect by the total control unit (host computer) 20.

A fifth point resides in that in step S412a, with regard to defect smaller than N of defects provided from the defect inspecting apparatus 2, an image of the defect is taken by the defect sampling magnification in correspondence with a dimension of the defect number n, and a defect image signal and a reference image signal are detected and inputted to the image inputting unit 13, subjected to processings of various corrections and noise component erasure and stored to the image storing apparatus 14 to thereby acquire the defect image signal and the reference image signal.

A sixth point resides in that in step S412b, the image processing apparatus 15 calculates a difference image signal showing defect between the defect image signal and the reference image signal acquired in step S412a, and detects a position (Xn', Yn') of the defect from the calculated difference image signal and a size of the defect calculated by an area and lengths in X and Y directions and so on from a binarized image signal indicating the defect.

A seventh point resides in that in step S412c, when the size of the defect detected in step S412b is larger than a size prescribed by HUGE II, the defect is not made an object of sampling image and the order is skipped to a successive defect. This is a processing of assuming a case in which there is no need of sampling and confirming image with respect to defect with a certain size or larger.

An eighth point resides in that in step S412d, the position (Xn', Yn') of the defect detected in step S412b is repositioned on the center of the field of view, image of the defect is taken with defect observing magnification in correspondence with the size of the defect which has been detected again, and the taken image signal is inputted to the image inputting unit 13 and stored to the image storing apparatus 14 after having been subjected to various corrections and noise component erasure to thereby acquire an image signal of large defect. In this way, the defect observing magnification in correspondence with a size of the defect for taking the image of the defect is made higher than the defect sampling magnification to thereby correspond to the size of the defect so that the image of the defect having higher resolution can be acquired. As a result, a digital image signal of small defect can be acquired with higher resolution by taking image with the defect observing magnification of, for example, 50,000 or more which is higher than the defect sampling magnification and therefore, the total control unit (host computer) 20 can classify large defect by further detailed analysis of characteristic amounts and properties of defect.

Figure 18:
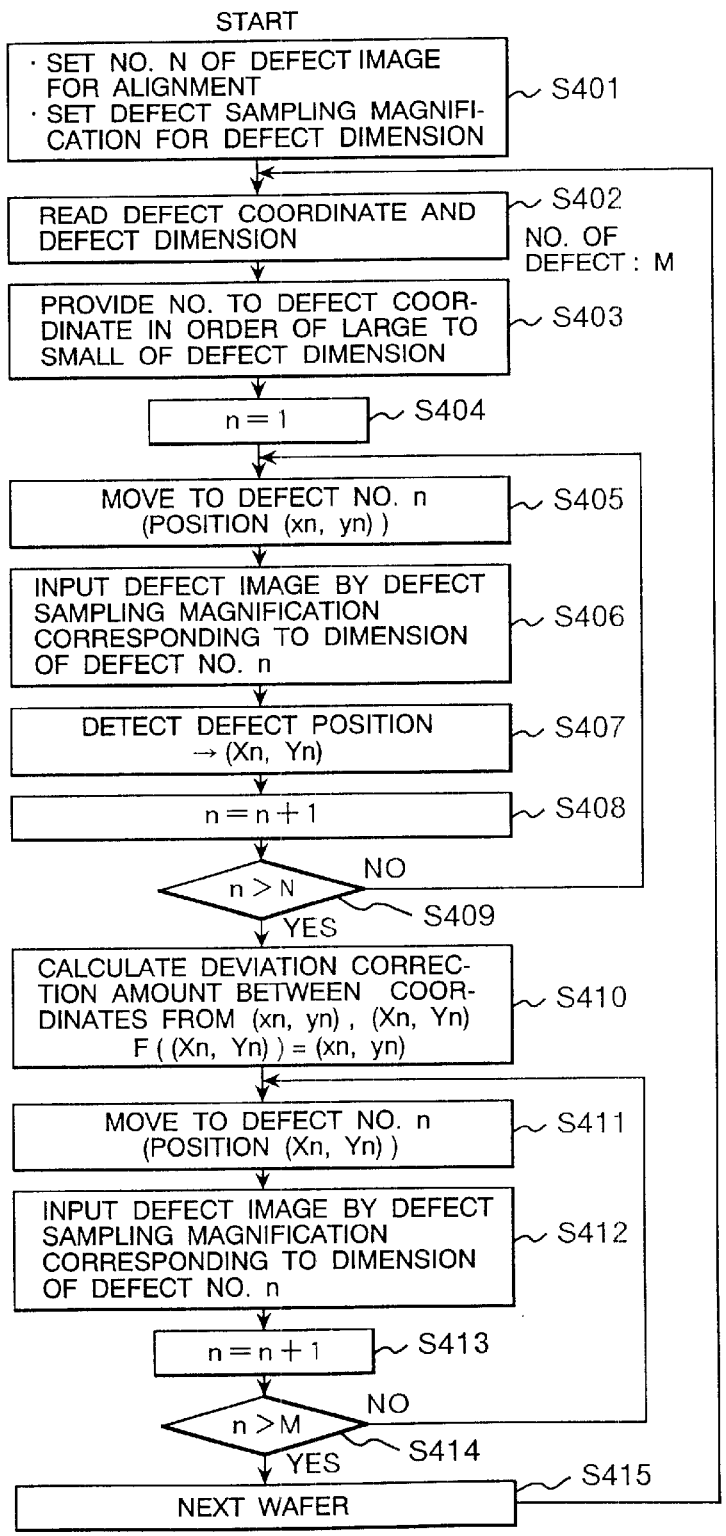
FIG. 18 is a flowchart diagram showing a first embodiment of subjecting image to automatic sampling processing in the automatic image sampling apparatus according to the present invention.

Other than the first through the eighth points described above, there is carried out operation and processing similar to those of the first embodiment shown in FIG. 18.

Further, data concerning dimensions of defects stored to the storing apparatus 23 and detected by the defect inspecting apparatus 2 can also be updated by data in respect of sizes of defects detected in step S412b and step S407a. Further, data concerning positions of defects detected in step S412 and step S407 are updated since they are more promoted than data concerning positions of defects detected by the defect inspecting apparatus 2 in view of accuracy.

Figure 19A:
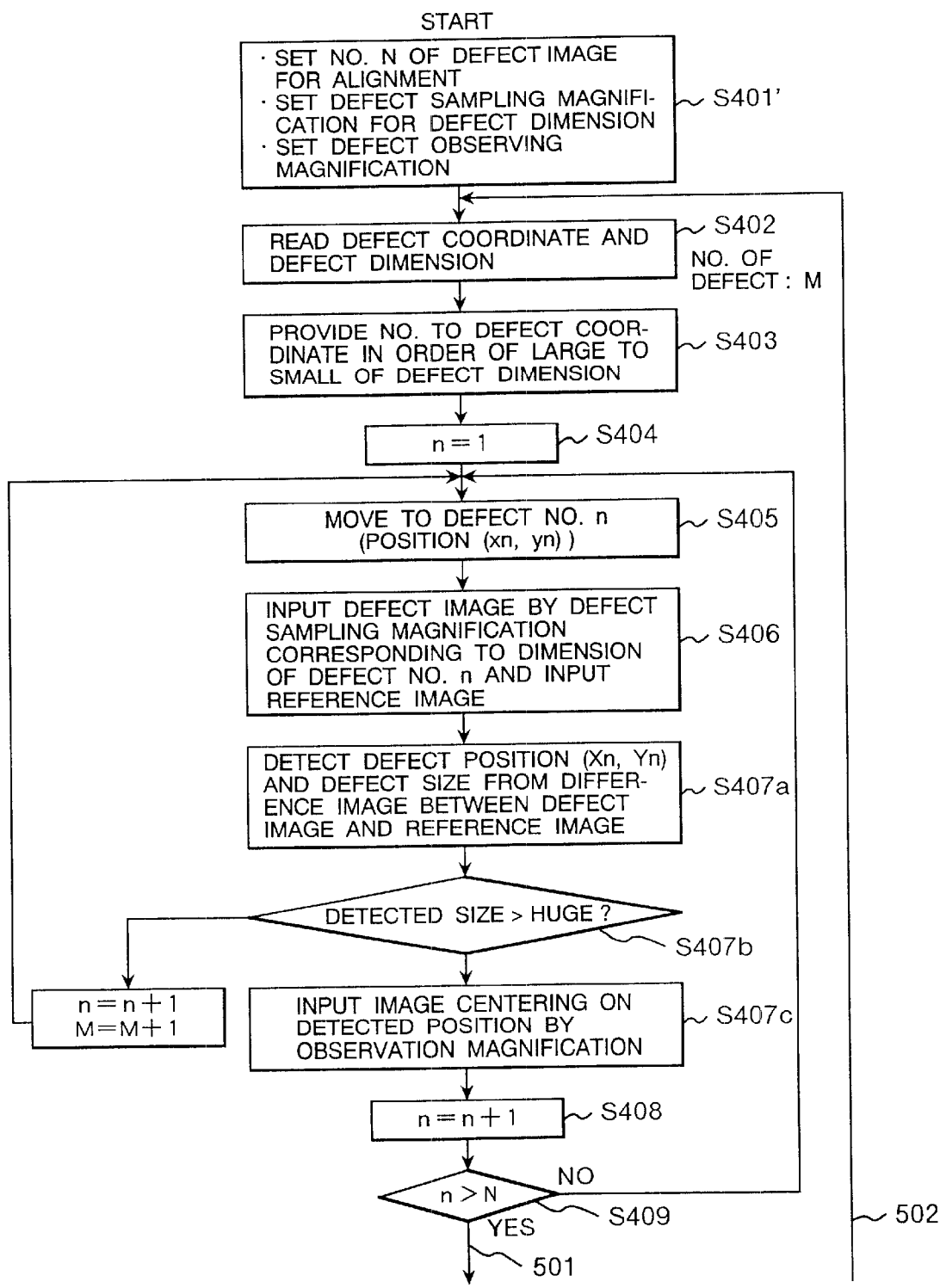
FIG. 19A is a flowchart diagram showing a former half of a second embodiment for subjecting image to automatic sampling processing in an automatic image sampling apparatus according to the present invention.
Figure 19B:
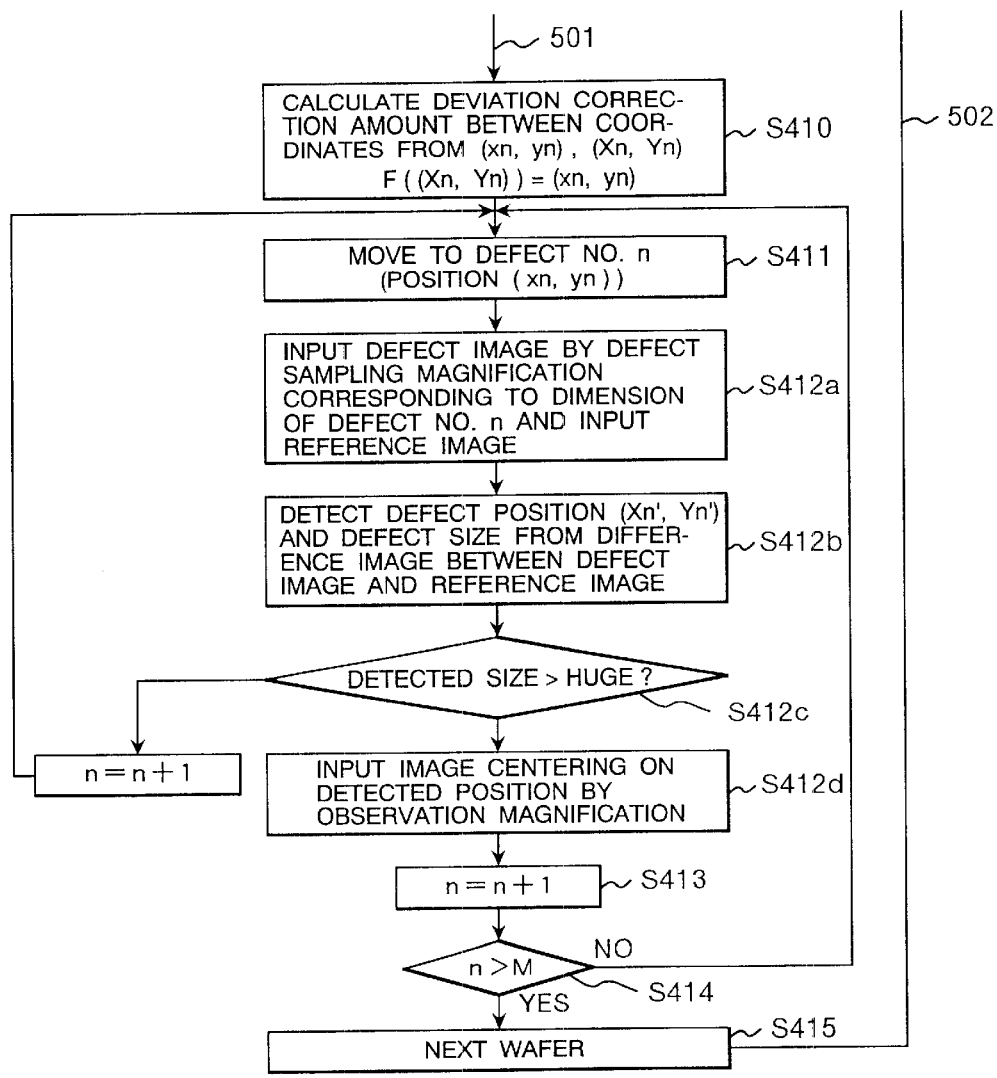
FIG. 19B is a flowchart diagram showing a latter half of the second embodiment for subjecting image to automatic sampling processing in the automatic image sampling apparatus according to the present invention.

Further, FIG. 19A and FIG. 19B are connected to each other by lines 501 and 502.

Further, steps S410 through S414 shown in FIG. 19B may be executed after a former half of steps S401 through S409 of FIG. 18 and a latter half of steps S410 through S414 shown in FIG. 18 may be executed after steps S401' through S409 shown in FIG. 19A.

FIG. 20 shows a number N (about 5 through 10) of large defects (size of large defect is mostly about 1 $\mu$m through 5 $\mu$m) used in alignment and defect sampling magnification (low magnification of about 3,000 to 7,000: about 10 through 30 $\mu$m as field of view of taking image) in carrying out alignment. The defect sampling magnification shows that in the automatic image sampling apparatus 3, based on position data detected by the defect inspecting apparatus 2, large defect present on the object substrate 10 can be positioned within field of view of taking image (about 10 through 30 $\mu$m) of low magnification of about 3,000 through 7,000. To be more specific, the defect sampling magnification shows a degree of error (about 10 through 25 $\mu$m or smaller) between the coordinate system of the automatic image sampling apparatus 3 and the coordinate system of the defect inspecting apparatus 2. Since a defect inspecting apparatus A is provided with defect sampling magnification of 3,000, positional accuracy of detected defect is the poorest and a defect inspection apparatus C is provided with defect sampling magnification of 7,000 and therefore, positional accuracy of detected defect is the most excellent.

In this way, since there is an error between the coordinate system of the automatic image sampling apparatus 3 and the coordinate system of the defect inspecting apparatus 2, in order to widen the field of view of taking image to about 10 through 30 $\mu$m such that defect can be positioned in the field of view of taking image, the image taking magnification needs to be low magnification of about 3,000 through 7,000. However, when the image taking magnification is made low magnification of about 3,000 through 7,000, the resolution is lowered and it becomes difficult to provide a digital image signal showing defect of, for example, about 1 $\mu$m or smaller. Hence, even when the resolution is lowered by making the image taking magnification to about 3,000 through 7,000, when image of defect having a size capable of recognizing position of the defect (about 1 $\mu$m through 5 $\mu$m) from a digital image signal provided by taking the image is taken, at least the position (Xn, Yn) of the defect can be detected, and the deviation correcting coefficients (A, B, C, D) shown by Equation (3), as mentioned above, can be calculated. Therefore, even when the defect sampling magnification is made high magnification of, for example, 10,000 or higher, the defect can be positioned (aligned) within the field of view of taking image. As a result, a digital image signal having high resolution based on high magnification can be acquired for the defect.

In each case, in the automatic image sampling apparatus 3, it is necessary to change a size of field of view of taking image, that is, image taking magnification (defect sampling magnification) necessary for alignment and a number of coordinates (number of alignment) N indicated by large defects depending on how coordinates are deviated at an initial state relative to those of the defect inspecting apparatus and on how the given coordinates are dispersed. These states are dependent on the defect inspecting apparatus 2 outputting information on coordinates of defects and therefore, as shown in FIG. 20, the defect sampling magnification in accordance with a dimension of defect and a number N of coordinates shown by large defects may be set and stored to the memory unit 24 for respective kinds of defect inspecting apparatus or respective defect inspecting apparatus. In this way, according to the total control unit (host computer) 20, information on so that defect inspecting apparatus the object substrate 10 charged into the automatic image sampling apparatus 3 has been inspected is inputted and stored to the storing apparatus 23 and accordingly, the defect sampling magnification (image taking magnification) in step S406 can be controlled for respective kinds of defect inspecting apparatus or respective defect inspecting apparatus.

Further, according to the total control unit (host computer) 20, by displaying on a monitor 18 a digital image signal provided by taking image with the defect sampling magnification in correspondence with the dimension of defect and stored to the image storing apparatus 14 in step S406 and step S412, it can be confirmed whether or not the defect sampling magnification and the number of coordinates N in accordance with dimensions of defects for respective kinds of defect inspecting apparatus or respective defect inspecting apparatus set and stored to the memory unit 24 are pertinent. Further, in this case, the total control unit 20 can display the table of the defect sampling magnification in accordance with dimensions of defects and the number of coordinates (number of alignment) N for respective kinds of defect inspecting apparatus or respect defect inspecting apparatus set and stored to the memory unit 24 on the monitor 18 and can modify them on the screen of the monitor 18 by using the inputting means 21 when they are impertinent.

Next, description will be given of a third embodiment of operation flow in which in order to recognize position of defect, an optimum defect size is selected, alignment is carried out in consideration also of a location of the defect on the object substrate (wafer) 10 and image of the defect is acquired with higher magnification with reference to FIG. 21A and FIG. 21B.

According to the third embodiment, the deviation correction coefficients [A, B, C, D] can be uniformly calculated over the whole are of the object substrate 10 by selecting the coordinate points (x″k, y″k) (k=1, . . . , K) of defect having defect dimensions most proximate to the designated defect dimension D on each of alignment blocks (n: n=1, . . . , N).

Figure 22A:
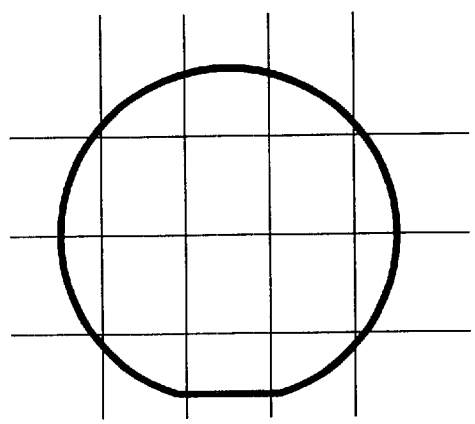
FIGS. 22(a) and 22(b) are views showing embodiments of dividing an inspection object into partitioned areas.
Figure 22B:
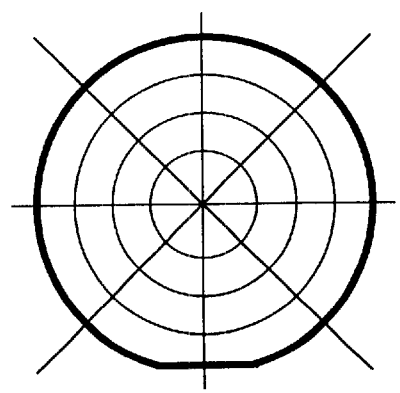

First, in step S501, there is set information concerning from which portion on the object substrate 10 defects on the object substrate 10 used for alignment are selected. It is preferable that the defects for alignment are uniformly arranged over a whole area of the object substrate 10. In order to realize this, as shown in FIGS. 22(a) and 22(b), the object substrate 10 is partitioned into a number of blocks and the defects for alignment having a predetermined number are selected from one block. Hereinafter, the block is referred to as an alignment block. Examples of the alignment blocks are shown in FIGS. 22(a) and 22(b). According to the example of FIG. 22(a), the object substrate 10 is partitioned vertically and horizontally in a shape of a lattice and one section thereof is made the alignment block. According to the example of FIG. 22(b), the object substrate 10 is partitioned by concentric circles and radial lines and one section thereof is made the alignment block. A predetermined number of the defects for alignment are selected from all of the alignment blocks or portions of the alignment blocks.

More specifically, information on the alignment blocks, that is, information on shape of the alignment block and sections to be used, a number N of blocks of the alignment blocks to be used and a number K of defects on the object subject 10 used for alignment which is set to one block, are previously set to store to the memory unit 24 of RAM or the like by inputting them by using the inputting means 21.

The image taking magnification (defect sampling magnification in respect of defect dimension) for sampling defect with defect dimension as a reference is set similar to the first embodiment.

Next, in step S501, a dimension D of defect on the object substrate 10 is previously set to store to the memory unit 24 of RAM or the like by inputting it by using the inputting means 21. Further, in respect of defect dimension data set to the memory unit 24 of RAM or the like, there are conceivable a method of defining the defect dimension by either of projected lengths in X and Y of detected image, that is, a larger one or a smaller one or an average of both, and a method of defining it by a diameter, a method of defining it by a dimension in a long axis or a dimension in a short axis when the detected image is approximated by an ellipse and so on in accordance with a definition of the defect dimension acquired from the defect inspecting apparatus 2.

Next, in step S502, position coordinates of defects in respect of defects having a number M on the object substrate 10 and information on dimension of defects which are inputted from the defect inspecting apparatus 2 to the automatic image sampling apparatus 3 are read by using the inputting means 21 of a record medium or the like and stored and accumulated to the storing apparatus 23.

Next, in step S503, the total control unit (host computer) 20 rearranges defects included in the respective alignment blocks in an order of large to small of dimensions thereof in respect of N of the alignment blocks designated by step S501 based on information concerning dimensions of defects with regard to defects having the number M on the object substrate 10 which are stored and accumulated to the storing apparatus 23 and charged to the automatic image sampling apparatus 3 and, in step 504, selects K of defects having defect dimensions most proximate to the designated defect dimension D and registers the selected order to the storing apparatus 23 as K-th defect coordinate points (x″k, y″k) in the alignment block n along with an alignment order k in the alignment block.

Further, the object substrate 10 is loaded on the stage 106 by the transfer apparatus 8.

Next, in step S505, the total control unit (host computer) 20 designates the alignment block number n as the order of alignment using defects on the object substrate 10 stored and accumulated to the storing apparatus 23 and inputted to the automatic image sampling apparatus 3 to be n=1 and, in step S506, designates the defect number k as the order of alignment of defects in the designated alignment block to be k=1.

Next, in step S507, the total control unit (host computer) 20 moves the stage 106 mounted with the object substrate 10 such that image of the defect positioned at coordinates (x″k, y″k) on the object substrate can be taken by the electron detector 120 by controlling to drive the stage control unit 16 and positions the defect based on the position coordinates of the defect from the alignment block order n=1 and the alignment defect order k=1 stored to the storing apparatus 23.

Next, in step S508, the total control unit (host computer) 20 selects the defect sampling magnification in correspondence with the dimension of the defect from the alignment block order n=1 and the alignment defect order k=1 stored to the storing apparatus 23 from the table set to the memory unit 24, controls to provide low magnification by switching the detecting system (112 etc.) to the low magnification detecting system to constitute the selected magnification or enlarging the scanning deflection amount by the scanning deflector 104 (may be combined with scanning of the stage 106) and takes image of the defect by low magnification. In this way, the defect having large dimension can be positioned within the field of view of taking image of low magnification and the position coordinates (x″k, y″k) of the defect can be detected by the coordinate system of the automatic image sampling apparatus 3. Further, in the case of the scanning electron microscope 101, the sampling period of digital conversion at the A/D converter 116 is made constant both in image taking at low magnification and image taking at high magnification. When the sampling period is made constant in this way, in the case of low magnification, a sampling interval is widened and the resolution is reduced in comparison with that in high magnification. However, the image taking magnification is determined in compliance with the dimension of the defect and accordingly, the same resolution can be provided in respect of the dimension of the defect. Further, the sampling period can be changed in accordance with the image taking magnification as necessary.

To be more specific, in step S508, according to the total control unit (host computer) 20, images of respective K of defects included in N of the alignment blocks are taken by the electron detector 120 with the defect sampling magnifications in correspondence with dimension of the defects by controlling the scanning deflection amount of the scanning deflector 104 (may be combined with scanning of the stage 106) such that the images are taken by the image taking magnifications in correspondence with the defect dimensions of respective K of the defects included in N of the alignment blocks set to the memory unit 24, inputted to the image inputting unit 13, converted into digital image signals at the image inputting unit 13, subjected to correction of dark level, correction of fluctuation of electron beam and correction of shading, subjected to filtering processing for erasing pseudo noise components and stored to the image storing apparatus 14. In this way, images of respective K of the defects included in N of the alignment blocks are taken by the coordinate system of the automatic image sampling apparatus 3 and accordingly, the operation also carries out alignment in the coordinate system of the automatic image sampling apparatus 3. The image taking magnification at this occasion may use fixed magnifications or variable magnifications (provided by controlling the scanning deflector 104 or the like) which are low magnifications set and stored to the memory unit 24 for taking the images of the defects for alignment.

Next, in step S509, based on instruction from the total control unit (host computer) 20, the images of respective K of the defects included in N of the alignment blocks set to the memory unit 24 are taken by the defect sampling magnifications in correspondence with the dimensions of the defects with, for example, an image at the same location of a contiguous chip as a difference image, inputted to the image inputting apparatus 13 and stored to the image recording apparatus (image storing apparatus) 14. As a result, the image processing apparatus 15 extracts difference images showing defects between the defect images and the difference images of respective K of the defects included in N of the alignment blocks stored to the image recording apparatus 14, converts the extracted difference images showing defects into, for example, binarized image signals and calculates, for example, center of gravity positions or central positions in X direction and Y direction from the converted binarized image signals showing defects so that positions of the defects in the image are detected and transmitted to the total control unit (host computer) 20. The control unit (host computer) 20 can convert the positions into positions in a reference coordinate system of the stage 106 measured by a position monitoring length measuring instrument (which is also a reference coordinate system on the object substrate 10 since the object substrate 10 is positioned and mounted onto the stage 106) based on position data of the defects in the image detected by the image processing apparatus 15 to thereby provide position coordinates $(X''k, Y''k)$ of the defects on the object substrate and can store them to the storing apparatus 23.

The total control unit (host computer) 20 provides (NXK) sets of coordinate pairs $[(x''k, y''k), (X''k, Y''k)]$ by instructing to repeat the above-described processings until k becomes K set to the memory unit 24 in step S511 and n becomes N set to the memory unit 24 in step S513. $(x''k, y''k)$ designates positions of the defects detected by the coordinate system of the defect inspecting apparatus (appearance inspecting apparatus) 2 and $(X''k, Y''k)$ designates positions of the defects detected by the coordinate system of the automatic image sampling apparatus 3 and a difference between the coordinates is accordingly a deviation of coordinate systems between the defect inspecting apparatus 2 and the automatic image sampling apparatus 3. Hence, in step S514, the total control unit (host computer) 20 derives a relationship equation between the coordinate systems by using (NK) sets of the coordinate pairs such that position coordinates of the defect inspecting apparatus 2 can be converted into position coordinates of the automatic image sampling apparatus 3. The conversion equation of $(x''k, y''k) \rightarrow (X''k, Y''k)$ is represented by Equation (3) shown by the first embodiment. The total control unit (host computer) 20 can calculate (A, B, C and D) from (MK) sets of the coordinate pairs $[(x''k, y''k), (X''k, Y''k)]$. As the calculating method, the offsets (C, D) are calculated from respective center of gravity positions of $(x''k, y''k)$ and $(X''k, Y''k)$ and thereafter, (A, B) may be calculated by the least square method utilizing pseudo inverse matrix. In this way, the total control unit (host computer) 20 can calculate the deviation correcting coefficients (A, B, C, D) in respect of the position coordinates $(x''k, y''k)$ of the defect inspecting apparatus 2 for calculating the position coordinates $(X''k, Y''k)$ of the automatic image sampling apparatus 3 based on Equation (3). According to above mention, the deviation correction coefficients [A, B, C, D] can be uniformly calculated over whole area of the object substrate for all alignment blocks N.

Next, in step S515, the total control unit (host computer) 20 determines the image taking order in respect of defects of the defect number M on the object substrate 10 stored and accumulated to the storing apparatus 23 and inputted to the automatic image sampling apparatus 3. Although according to the first embodiment and the second embodiment, the image taking order has been described as the order of dimensions of defects, there is no guarantee that the order is optimized in view of a total distance of movement of the stage for taking images of all the defects. There is the advantage of capable of shortening a total time period of taking images of defects by determining an order of observing defects under a reference for minimizing the stage moving distance. The shortest path connecting a plurality of points on a plane at predetermined positions can be calculated by a method disclosed in, for example, Isato, Koshizuka "bit supplement, Calculus Geometry and Geographical Information Processing" pp110–121, Kyoritsu Shuppan (1986). The total control unit (host computer) 20 determines the order of taking images of defects in accordance with the reference of minimizing the stage moving distance, as mentioned above, in respect of the defect position coordinates (xn, yn) stored to the storing apparatus 23 and provided from the defect inspecting apparatus 2 with respect to M of the defects and registers the rearranged order as the image sampling order n at the automatic image sampling apparatus 3. Further, a number of defects on the object substrate 10 charged into the automatic image sampling apparatus 3 is M and accordingly, a number of defects constituting objects of image taking at the automatic image sampling apparatus 3 becomes M.

Next, in step S516 (S410), deviation correction is carried out by using the conversion equation shown by Equation (3), as mentioned above, and the defect position coordinates (Xn, Yn) on the object substrate 10 in the coordinate system of the automatic image sampling apparatus 3 are calculated. Further, the object substrate 10 is loaded on the stage 106 by the transfer apparatus 8.

Next, in step S517, the total control unit (host computer) 20 designates n=1 as the image sampling order n of defects on the object substrate 10 stored and accumulated to the storing apparatus 23 and inputted to the automatic image sampling apparatus 3.

Next, in step S518 (S411), the total control unit (host computer) 20 moves the stage 106 mounted with the object substrate 10 such that image of the defect n positioned at (xn, Yn) on the object substrate can be taken by the electron detector 120 by controlling to drive the stage control unit 16 based on the position coordinates of the defect from the defect number n=1 stored to the storing apparatus 23 to thereby position the defect n on the optical axis.

Next, in step S519 (S412), the total control unit (host computer) 20 selects the defect sampling magnification in correspondence with the defect dimension from data of the defect number n=1 stored to the storing apparatus 23 from the table set to the memory unit 24 and controls to provide the observing magnification by switching the detecting system (112 etc.) to the low magnification detecting system to constitute the selected magnification or enlarging the scanning deflection amount by the scanning deflector 104 (may be combined with scanning of the stage 106) so that the image of the defect is taken.

Next, in step S520 (S413), a successive defect (n=n+1) is designated in accordance with the image sampling order. In step S521 (S414), input of image is finished with respect to all of the defects present on the object substrate. Then, in step S522 (S414), the object substrate 10 is unloaded on the stage 106 by the transfer apparatus 8 and the operation proceeds to taking image of defect of a successive object substrate. In this way, as the image taking for M of defects can be realized by the route being shortened, a time of the image taking can be reduced.

Although according to the above-described explanation, it has been described that image is taken with the defect sampling magnification in correspondence with the defect dimension (defect size) based on the correlation table between the defect dimension and the image taking magnification stored to the memory unit 24, for example, in taking image of defect for alignment, a first fixed image taking magnification may be used and in taking image of defect other than the above-described case, that is, in taking image of defect in step S519, a second fixed image taking magnification may be used. At this occasion, as mentioned above, further detailed position deviation correction can be carried out by using defects images of which are taken by the first image taking magnification for alignment, as mentioned above, positioning accuracy (alignment accuracy) of defect in taking images of defects in step S519 can be promoted. As a result, dispersions from centers of fields of view of images of defects after positioning are reduced and image can be taken by a field of view narrower than a field of view provided by the first image taking magnification, that is, higher magnification by the second image taking magnification. To be more specific, the second image taking magnification can be set to magnification higher than the first image taking magnification. By setting the second image taking magnification to magnification higher than the first image taking magnification, finer defect can also be caught on the image with high resolution and characteristic amounts (size, shape, surface texture, gray scale value and so on) of the finer defect can accurately be sampled and the defect can be classified by detailed analysis in respect of properties (categories) of the defect. Particularly, by setting the second image taking magnification to as high magnification as possible (for example, 50,000 (image can be taken as a digital image signal with a ratio of 0.02 μm to 1 mm) through 30,000 (image can be taken as a digital image signal with a ratio of 0.02 μm to 0.6 mm) or more), characteristic amounts of defect can more accurately be sampled and the defect can be classified by analyzing properties (categories) of the defect further in details.

Although according to the above-described specific example, an explanation has been given of the case in which the image taking magnification is switched in two stages in accordance with the object of taking image of defect, as mentioned above, the classification may be carried out in accordance with the defect dimension (defect size) and the image taking magnification may be determined in accordance with a class of the defect dimension. Further, there may be adopted a method of applying image taking magnification for taking image by image size (unit: pixel) so that the size of defect observed on the image is previously designated.

Figure 21A:
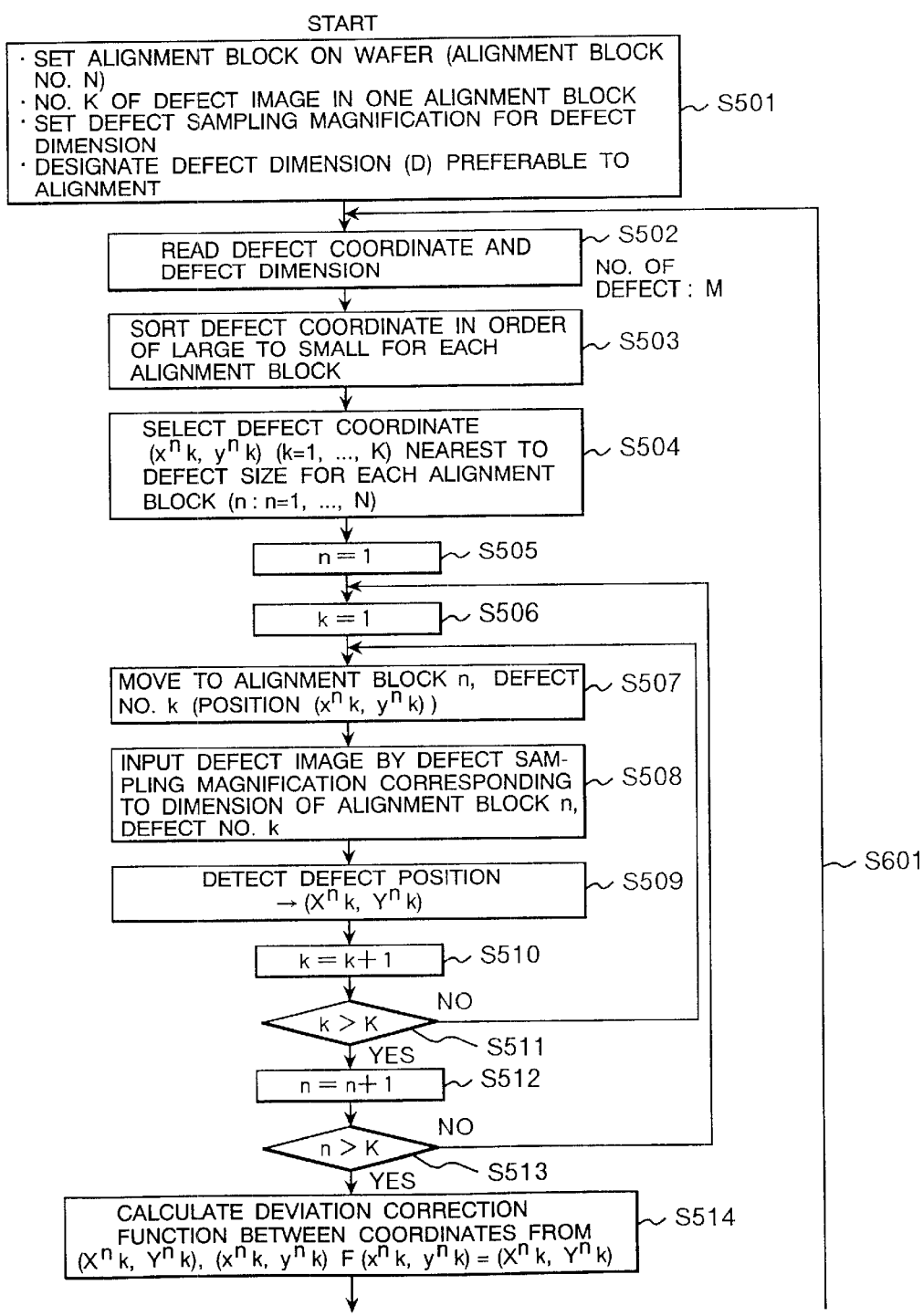
FIG. 21A is a flowchart diagram showing a former half of a third embodiment for subjecting image to automatic sampling processing in the automatic image sampling apparatus according to the present invention.
Figure 21B:
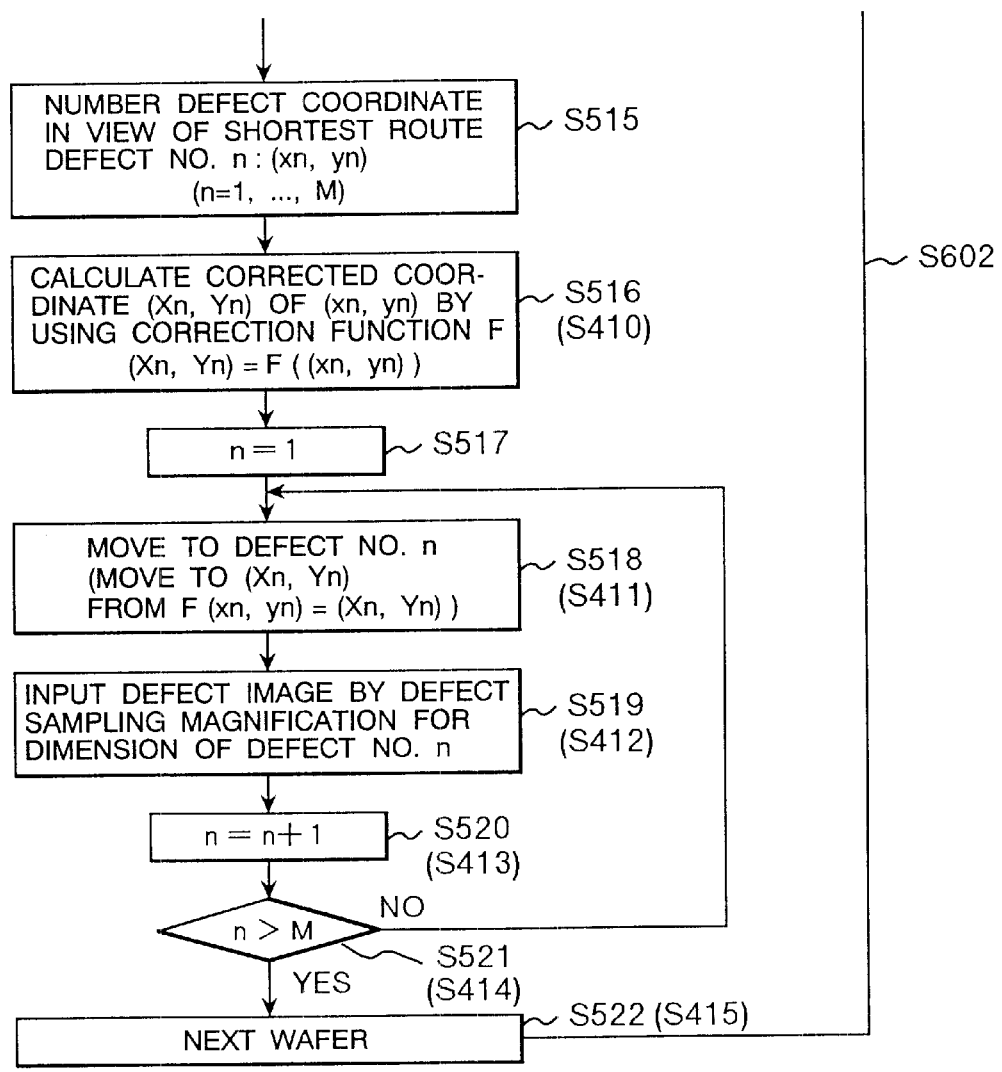
FIG. 21B is a flowchart showing a latter half of the third embodiment shown in FIG. 21A.

Further, FIG. 21A and FIG. 21B are connected to each other by lines 601 and S602.

Next, description will be given of points of a fourth embodiment which differ from the third embodiment shown in FIGS. 21A and, 21B of operation flow shown in FIG. 23A and FIG. 23B for acquiring defect images with higher magnification based on position coordinates of defects, a number of defects on an object substrate and dimension of defects provided from the defect inspecting apparatus 2.

First, a first point resides in correcting the coordinate system transmitted from the inspecting apparatus 2 by using a pattern for alignment formed on the object substrate 10 in step S504a. The alignment pattern is formed by utilizing a fabrication process similar to that of an electronic circuit pattern formed on the object substrate 10 and formed by a geometrical pattern having symmetry such as a circle, a square or a cross to facilitate to confirm its central position. By using at least two of alignment patterns at different positions, the coordinate conversion coefficients (A, B, C, D) for converting (x, y)→(X, Y) can be calculated by using Equation (3) from position coordinates (x, y) of the alignment marks in the inspecting apparatus 2 and position coordinates (X, Y) in the automatic image sampling apparatus 3 and a coordinate conversion function G: G (x, y)=(X, Y) for converting (x, y)→(X, Y) can be determined.

A second point resides in that in step S507', the total control unit (host computer) 20 corrects position coordinates of the defect from the alignment block order n=1 and the alignment defect order k=1 stored to the storing apparatus 23 by the coordinate conversion function G derived in step 504a and controls to drive the stage control unit 16 based on the corrected position coordinates so that the defect is positioned by moving the stage 106 mounted with the object substrate 10 such that the image of the defect positioned at G ($x''k$, $y''k$) on the object substrate can be taken by the electron detector 120. By the coordinate conversion function G, positioning accuracy (alignment accuracy) of defect for alignment can be promoted, as a result, a dispersion from the center of the field of view of image of defect at the position is reduced and alignment can be carried out firmly.

A third point resides in that in step S517', the total control unit (host computer) 20 stores and accumulates both of offset values for each of X and Y, offsetx and offsety as 0 to the storing apparatus 23.

A fourth point resides in that in step S518', the total control unit (host computer) 20 positions the defect n by moving the stage 106 mounted with the object substrate 10 such that image of the defect n positioned at (Xn+offsetx, Yn+offsety) on the object substrate can be taken by the electron detector by controlling to drive the stage control unit 16 based on position coordinates of the defect from the defect number n=1 stored to the storing apparatus 23 to thereby position the defect n at the optical axis.

A fifth point resides in that in step S519a, the image processing apparatus 15 calculates a difference image signal showing defect by using, for example, a reference image signal from the acquired defect image signal and detects position (Xn', Yn') of the defect from the calculated difference image signal.

A sixth point resides in that in step S519b, the offset (offsetx, offsety) is calculated from a difference between the position (Xn', Yn') of the defect calculated in step 519a and the position (Xn, Yn) of the defect calculated by using the correction function in step 516.

The offset mentioned at the third point, the fourth point, the fifth point and the sixth point represents a deviation between the defect coordinate value provided by processing it by the coordinate connection function F provided by alignment and a true defect coordinate value provided by the image by actually providing the image of the defect. The defect is based on a way of thinking of minimizing movement of the stage and accordingly, according to the observation order, defects of contiguous two points are present comparatively proximate to each other. Accordingly, when the provided offset is used in positioning a successive defect, the defect can be positioned further accurately.

Other than the first through the sixth points described above, the same operation and processing as those in the third embodiment shown in FIGS. 21A and 21B are carried out.

Figure 23A:
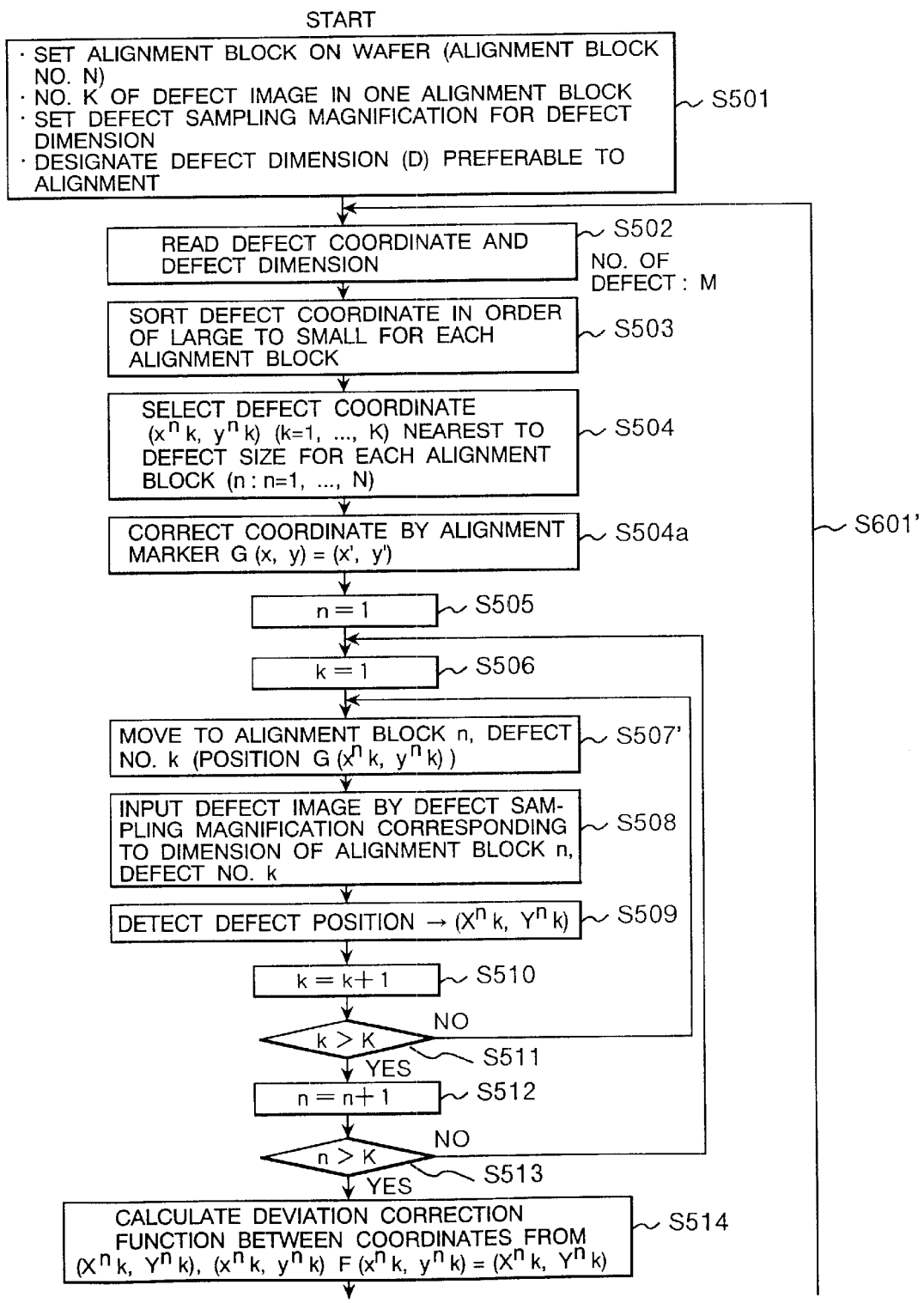
FIG. 23A is a flowchart diagram showing a former half of a fourth embodiment of subjecting image to automatic sampling processing in an automatic image sampling apparatus according to the present invention.
Figure 23B:
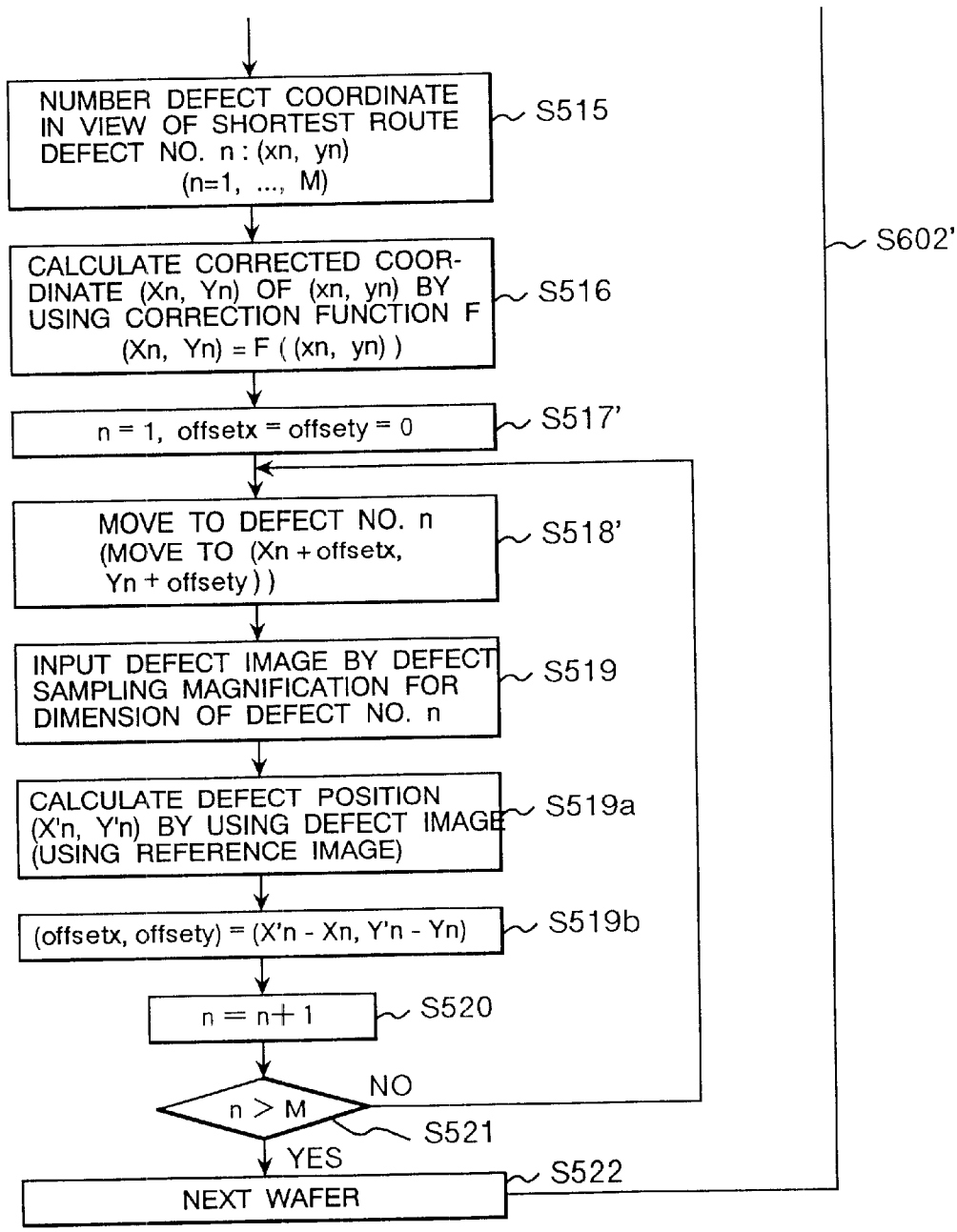
FIG. 23B is a flowchart showing a latter half of the fourth embodiment shown in FIG. 23A.

Further, FIGS. 23A and FIG. 23B are connected by lines S601'and S602'.

Further, steps S515 through S522 shown in FIG. 23B may be executed after a former half of steps S501 through S514 shown in FIG. 21A and steps S515 through S522 of a latter half shown in FIG. 21B may be executed after steps S501 through S514 shown in FIG. 23A.

As mentioned above, although in the automatic image sampling apparatus 3, an explanation has been given of the embodiments of setting the image taking magnification of image in accordance with the dimension of defect, the image taking magnification of image may be determined in accordance with a kind of a circuit pattern formed at a portion on object substrate (wafer substrate) constituting the object of taking image. The circuit pattern on the object substrate such as a semiconductor wafer or the like is fine, and lowering of the image magnification signifies lowering of the sampling frequency when the circuit pattern is caught by a digital image. Therefore, when the sampling frequency becomes a half or smaller of a spatial frequency of the circuit pattern formed on the object substrate, there is a concern that a pattern of a kind of an interference fringe which is not originally present on the object substrate is superposed by aliasing so that defect becomes difficult to observe. Therefore, at a portion of the circuit pattern having high spatial frequency, the image taking magnification (defect sampling magnification, defect observing magnification) needs to set high and at a portion thereof having low spatial frequency, the image taking magnification (defect sampling magnification, defect observing magnification) needs to set low. Accordingly, the above-described noise pattern by aliasing can be prevented from being produced by prescribing the image taking magnification of image for respective areas on the object substrate. Accordingly, it is necessary for the total control unit (host computer) 20 that design information concerning kinds of circuit patterns formed at respective partial areas on the charged object substrate 10 is previously inputted from the CAD system 1206 (shown in FIG. 2) or the management system 1205 (shown in FIG. 2) by using the inputting means 21 of a record medium or the like or the network 22 and stored to the memory unit 24 or the storing apparatus 23. Further, the total control unit (host computer) 20 can, previously confirm whether or not the image taking magnification (defect sampling magnification, defect observing magnification) for respective area of the charged object substrate 10 is pertinent by calculating lowest image taking magnification for the respective areas of the object substrate 10 and storing it to the memory unit 24 based on design information concerning kinds of the circuit patterns (spatial frequency).

To be more specific, the total control unit (host computer) 20 can output the lowest image taking magnification of the area from the memory unit 24 by position coordinates of defects detected by the defect inspecting apparatus 2 and stored to the storing apparatus 23. Therefore, the total control unit 20 can investigate on whether or not the defect sampling magnification in correspondence with the dimension of defect in step S406 and steps S412 and S412a and the defect observing magnification in step S407c and step S412d satisfy the condition of the lowest image taking magnification in an area where defect is present. When the condition is not satisfied, sampling of image of the defect is skipped in steps being the same as steps S407b and S412c for skipping to sample image of defect in accordance with the size of defect shown in FIGS. 19A and FIG. 19B. In this way, the total control unit 20 can acquire a digital image signal honestly showing defect by preventing noise pattern from a background (circuit pattern) of defect from being produced by taking image of defect by satisfying the minimum image taking magnification in an area where defect is present with respect to the defect sampling magnification or the defect observing magnification, can accurately carry out deviation correction (alignment) and can promote reliability of detailed analysis with respect to characteristic amounts and properties of defect.

As has been explained, according to the present invention, even when a sample for image taking, a magnification for image taking and a period in digital sampling are changed, image of the sample can accurately be taken without causing pseudo noise under respective conditions.

Further, according to the present invention, even when any object substrate is taken by any magnification, there is achieved an effect in which image can be accurately taken automatically without causing pseudo noise in the provided digital image, position of defect portion can be specified and characteristic amounts or properties of the defect portion can be analyzed for the defect portion.

Further, according to the present invention, a difference of coordinate systems present between the apparatus of the present invention and a defect inspecting apparatus can stably be corrected and accordingly, even fine defect detected by the defect inspecting apparatus can stably be caught in a short period of search time, as a result, there is achieved an effect of realizing the automatic image sampling apparatus and the method by the scanning electron microscope capable of acquiring a digital image signal having high resolution taken at high image taking magnification (for example, 10,000 or higher) capable of carrying out detailed analysis in respect of characteristic amounts:(size, shape, surface texture, gray scale value) and properties (categories) of the defect.

What is claimed is:

1. The scanning electron microscope comprising:

a stage for mounting an object substrate;

an electron gun for emitting electron beam;

a converging lens for converging the electron beam emitted from the electron gun;

scanning unit for two-dimensionally scanning a surface of the object substrate with the electron beam converged by the converging lens;

an objective lens for focusing the electron beam converged by the converging lens in a spot-like shape on the surface of the object substrate;

a detector for detecting an intensity of at least one of secondary electron or reflected electron or absorbed electron generated from the object substrate by scanning with the electron beam by the scanning unit and outputting an analog image signal;

an A/D conversion unit for sampling the analog image signal detected by and outputted from the detector and converting the analog image signal into a digital image signal;

a switching control unit for controlling to switch at least the scanning unit so that a digital image signal having a low magnification based on a wide image taking field of view and a digital image signal having a high magnification based on a narrow image taking field of view are provided to be switched from the A/D conversion unit; and a beam spot diameter control unit for controlling to switch a spot diameter of the electron beam at the surface of the object substrate in accordance with the magnification when the scanning unit is controlled so as to switch by the switching control unit.

2. The scanning electron microscope according to claim 1, wherein the beam spot diameter control unit controls a spot diameter of the electron beam based on information concerning a surface texture at a portion of the object substrate for taking an image when the detector takes the image with the wide image taking field of view by controlling so as to switch the scanning unit by the switch control unit.

3. The scanning electron microscope according to claim 1 or 2:

wherein the beam spot diameter control unit is constituted to control to move the stage in a direction of irradiating with the electron beam.

4. The scanning electron microscope according to claim 1 or 2:

wherein the beam spot diameter control unit is constituted by controlling the objective lens.

5. The scanning electron microscope according to claim 1 or 2:

wherein the beam spot diameter control unit is constituted by controlling current of the electron beam emitted from the electron gun.

6. The scanning electron microscope according to claim 1, further comprising:

a control unit for controlling to restrain pseudo noise components generated from a portion of the object substrate for taking an image when the detector takes the image with the wide image taking field of view by controlling so as to switch the scanning means by the switching control unit.

7. The scanning electron microscope according to claim 1, further comprising:

a signal processing unit for reducing pseudo noise components at high frequencies by carrying out a signal processing in accordance with a surface texture at a portion of the object substrate for an analog image signal outputted from the detector when the detector takes an image with the wide image taking field of view by controlling so as to switch the scanning unit by the switching control unit.

8. The scanning electron microscope according to claim 1, further comprising:

a signal processing unit for reducing pseudo noise components at high frequencies by carrying out a signal processing in accordance with a surface texture of a portion of the object substrate for a digital image signal provided by the A/D conversion unit when the detector takes an image with the wide image taking field of view by controlling so as to switch the scanning unit by the switching control unit.

9. The scanning electron microscope according to claim 7 or 8:

wherein the signal processing unit is constituted to carry out a filtering signal processing.

* * * * *